US012779092B2

(12) United States Patent
Zhuang et al.

(10) Patent No.: US 12,779,092 B2
(45) Date of Patent: Nov. 3, 2026

(54) HYALURONIC ACID-BASED HYDROGEL PRECURSOR SOLUTION, HYALURONIC ACID-BASED HYDROGEL AND REPAIR MATERIAL THEREOF

(71) Applicant: SUN YAT-SEN UNIVERSITY, Guangdong (CN)

(72) Inventors: Lin Zhuang, Guangdong (CN); Xiaolei Li, Guangdong (CN); Wuming Liu, Guangdong (CN)

(73) Assignee: SUN YAT-SEN UNIVERSITY, Guangdong (CN)

( * ) Notice: Subject to any disclaimer, the term of this patent is extended or adjusted under 35 U.S.C. 154(b) by 362 days.

(21) Appl. No.: 18/587,913

(22) Filed: Feb. 26, 2024

(65) Prior Publication Data

US 2025/0135070 A1 May 1, 2025

(30) Foreign Application Priority Data

Oct. 31, 2023 (CN) ......................... 202311435394.9

(51) Int. Cl.
*A61L 27/52* (2006.01)
*A61L 27/20* (2006.01)

(52) U.S. Cl.
CPC ............... *A61L 27/52* (2013.01); *A61L 27/20* (2013.01); *A61L 2400/04* (2013.01); *A61L 2430/02* (2013.01); *A61L 2430/34* (2013.01)

(58) Field of Classification Search
CPC ....................................................... A61L 27/52
See application file for complete search history.

(56) References Cited

U.S. PATENT DOCUMENTS

2022/0118124 A1* 4/2022 Yang ...................... A61K 47/58

OTHER PUBLICATIONS

Xiaohu Liu et al., "Effect of Temperature and Accelerator on Gel Time and Compressive Strength of Resin Anchoring Agent", Advances in Polymer Technology, Sep. 2019, pp. 1-12.

Qinchao Zhu et al., "White-light crosslinkable milk protein bioadhesive with ultrafast gelation for first-aid wound treatment", Biomaterials Research, Feb. 2023, pp. 1-18.

* cited by examiner

*Primary Examiner* — Genevieve S Alley
(74) *Attorney, Agent, or Firm* — JCIPRNET

(57) ABSTRACT

The present invention relates to a hyaluronic acid-based hydrogel precursor solution, a hyaluronic acid-based hydrogel, a preparation method and a repair material thereof. The hyaluronic acid-based hydrogel precursor solution includes a component A and a component B; the component A is prepared by the following steps: step S1, mixing methacrylate group-modified hyaluronic acid with furfuryl amine for reaction, to obtain furan-methacrylate modified hyaluronic acid; step S2, mixing the furan-methacrylate modified hyaluronic acid with maleimide for reaction, to obtain hyaluronic acid modified with dual groups; and step S3, mixing the hyaluronic acid modified with dual groups with a photoinitiator and a solvent, to obtain the component A; and the component B is a mercapto polyethylene glycol solution.

14 Claims, 21 Drawing Sheets
(7 of 21 Drawing Sheet(s) Filed in Color)

HYALURONIC ACID-BASED HYDROGEL PRECURSOR SOLUTION, HYALURONIC ACID-BASED HYDROGEL AND REPAIR MATERIAL THEREOF

CROSS-REFERENCE TO RELATED APPLICATION

This application claims the priority benefit of China application serial no. 202311435394.9, filed on Oct. 31, 2023. The entirety of the above-mentioned patent application is hereby incorporated by reference herein and made a part of this specification.

BACKGROUND

Technical Field

The present invention relates to the technical field of biomedical materials, and more specifically relates to a hyaluronic acid-based hydrogel precursor solution, a hyaluronic acid-based hydrogel, a preparation method and a repair material thereof.

Description of Related Art

Maxillofacial region is an important part for keeping normal physiological activity and conveying emotional message; its skeleton and skin are basis for human body's aesthetics. The bone of maxillofacial region plays a moving and supporting role for human body. As an external barrier, the skin of maxillofacial region protects internal tissues and organs from external physical and chemical damages and microbial invasion while embodying facial aesthetics.

The composition and structure of maxillofacial region are complex; therefore, when maxillofacial region is damaged, defects will simultaneously occur in tissues such as jawbone, skin and blood vessel. For example, defect of dentition, external injury, orofacial clefts, etc. will often cause the defect of jawbone. Traditional therapeutic methods for jawbone defect include distraction osteogenesis, guided tissue regeneration, bone graft, etc. Even though these methods promote osteogenesis and reduce the difficulty of orthodontics or orthognathic surgery, there are still lots of limitations such as complicated operation, poor adaptation, donor shortage, immunological rejection, and expensive cost. In recent years, people also have achieved great breakthrough on artificially-synthesized bone tissue scaffold materials, but the poor osteoinduction capability of bone tissue scaffold materials still have to be settled urgently. Bio-components (e.g., cells cultured ex vivo, growth factors, BMP2 protein, and RGD sequence) are added to bone tissue scaffold materials, which has a potential value to increase the effect of osteoinduction. However, in clinical application, these tissue engineering materials containing bio-components will be restricted by complex regulations of drug, and have very expensive use costs at the same time. Therefore, in terms of experimental study, clinical transformation and commercialized production, if a bone tissue scaffold material can be free of bio-components itself and has strong osteoinduction capability, and can recruit body's cells for osteanagenesis, it has very remarkable advantages in bone tissue engineering.

External cause of injury, congenital malformation, surgery, and the like will cause skin defect of maxillofacial region, scar hypertrophy, morphological abnormality, and functional defect, thus seriously affecting appearance and living quality. Most of dermal injury wounds can be self-healed, but have a slow healing process and limited healing degree, and cannot achieve the complete regeneration and reconstruction of the intact skin tissues.

If a material can not only be used as a bone tissue scaffold material to induce osteanagenesis, but also serve as a dressing to accelerate skin repairing, it has a very high value in the treatment of combined soft and sclerous tissues injuries of maxillofacial region. In a Chinese patent titled a hyaluronic acid supramolecular hydrogel for use in three-dimensional culture of chondrocytes, preparation and use thereof, functional groups poly di(ethylene glycol)methylether methacrylate (PDEGMA) in response to temperature and ureido pyrimidone (UPy) are introduced into the hyaluronic acid backbone; the obtained hyaluronic acid supramolecular hydrogel has the ability of promoting chondrogenesis. However, in the patent, the study on the repair mechanism of bone tissues is still not profound enough, and skin repairing is not concerned such that its application prospect is unknown in the treatment of combined soft and sclerous tissues injuries of maxillofacial region.

Additionally, macrovascular hemorrhage often occurs in the maxillofacial impairment caused by an injury (e.g., traffic accident and wartime wound); therefore, it is of great importance to achieve the rapid hemostasis of wounds. At present, hydrogel has been commonly used in the treatment of injuries. As for hemorrhage and other situations in the maxillofacial impairment, the hydrogel should meet the following requirements in its use: (1) the hydrogel precursor solution has a high mobility and can be sprayed such that the entire surface of the wound can be directly covered according to the conditions (e.g., shape) of the maxillofacial wound, easy to use; (2) the hydrogel precursor solution can achieve rapid gelation; and (3) low hemolysis ratio and good hemostatic function. Currently, there are still a few of hydrogels meeting the above requirements simultaneously; for the point (2), the existing hydrogel precursor solution has a gelation time (under direct UV irradiation) of greater than 10 s generally (for example, X. H. Liu, Z. S. Yao, W. P. Xue, X. Li, Effect of Temperature and Accelerator on Gel Time and Compressive Strength of Resin Anchoring Agent, Adv. Polym. Technol. 2019 (2019), or Q. C. Zhu, X. H. Zhou, Y. A. Zhang, D. Ye, K. Yu, W. B. Cao, L. W. Zhang, H. W. Zheng, Z. Y. Sun, C. C. Guo, X. Q. Hong, Y. Zhu, Y. J. Zhang, Y. Xiao, T. G. Valencak, T. C. Ren, D. X. Ren, White-light crosslinkable milk protein bioadhesive with ultrafast gelation for first-aid wound treatment, *Biomaterials Research* 27(1) (2023)). Longer gelation time is not good for the rapid hemostasis of wound.

Therefore, it needs to develop a sprayable material which is capable of achieving rapid gelation for wound hemostasis, and has bone and skin defect repair capabilities, thus providing an integrated therapeutic scheme for the combined injuries of maxillofacial soft and sclerous tissues, which is of great significance.

SUMMARY

The primary object of the present invention is to overcome the technical problem mentioned in the above prior art, and to provide a hyaluronic acid-based hydrogel precursor solution.

A further object of the present invention is to provide a preparation method of the above hyaluronic acid-based hydrogel precursor solution.

A further object of the present invention is to provide a hyaluronic acid-based hydrogel.

A further object of the present invention is to provide use of the above hyaluronic acid-based hydrogel precursor solution or the hyaluronic acid-based hydrogel in the preparation of a repair material for treating a maxillofacial combined injury.

The above objects of the present invention will be achieved by the following technical solutions.

A hyaluronic acid-based hydrogel precursor solution is provided, including a component A and a component B; the component A is prepared by the following steps:

step S1, mixing methacrylate group-modified hyaluronic acid with furfuryl amine for reaction, to obtain furan-methacrylate modified hyaluronic acid;

step S2, mixing the furan-methacrylate modified hyaluronic acid with maleimide for reaction, to obtain hyaluronic acid modified with dual groups; and step S3, mixing the hyaluronic acid modified with dual groups with a photoinitiator and a solvent, to obtain the component A;

where the component B is a mercapto polyethylene glycol solution, and a mass ratio of the component A to the component B is 1:(2.5-5.0).

According to the hyaluronic acid modified with dual groups in the component A of the hyaluronic acid-based hydrogel precursor solution of the present invention, firstly, a furan group is grafted onto the methacrylate group-modified hyaluronic acid, and reacts with maleimide to form a norbornene-like group, so as to obtain hyaluronic acid having two photocrosslinked groups including the methacrylate group and the norbornene-like group, i.e., the hyaluronic acid modified with dual groups. The hyaluronic acid-based hydrogel precursor solution (after the component A and the component B are mixed) has a very high mobility, and can be not only injected, but also sprayed. In combination with the hyaluronic acid modified with dual groups, photoinitiator, and mercapto polyethylene glycol, the hyaluronic acid-based hydrogel precursor solution can not only achieve rapid self-healing rate (0.5 s) for gelation which is ahead of the existing hydrogel material under direct UV irradiation, but also can achieve slow self-healing for gelation under UV light-free conditions. Moreover, the hyaluronic acid-based hydrogel obtained after gelatinizing the hyaluronic acid-based hydrogel precursor solution has good mechanical properties and swelling properties.

It has been found by the inventor of the present invention through further studies that the hyaluronic acid-based hydrogel precursor solution and the gelatinized hydrogel of the present invention have a variety of biological properties. Firstly, the hyaluronic acid-based hydrogel not only has the inherent physical guidance functions of a hydrogel, but also has bioinduction functions, thus possessing a good bone defect repair capability. Secondly, the hyaluronic acid-based hydrogel precursor solution and the gelatinized hydrogel can activate exogenous and endogenous pathways in coagulation cascade reactions by promoting blood platelet adsorption and erythrocyte aggregation; and can achieve ex vivo and in vivo rapid hemostasis by forming a physical barrier via the transformation of an aqueous phase into a gel phase. Thirdly, the hyaluronic acid-based hydrogel can facilitate the healing of skin defect in each stage, including adjustment and control of macrophage differentiation in the inflammatory stage, accelerating neovascularization in the proliferative stage and accelerating fibroblasts to secrete extracellular matrix in the remolding stage, which achieves immunoregulation and accelerates neovascularization, thus promoting the repairing of skin defect.

The hyaluronic acid-based hydrogel precursor solution of the present invention can be sprayed and has a rapid gelation rate and hemostatic functions, and has bone and skin defect repair capabilities at the same time. Therefore, the hyaluronic acid-based hydrogel precursor solution of the present invention can provide an integrated therapeutic scheme for the combined injuries of maxillofacial soft and sclerous tissues, and thus has a good application prospect.

It should be understood that the methacrylate group-modified hyaluronic acid in the step S1 refers to hyaluronic acid grafted with a methacrylate group after the modification.

Preferably, the methacrylate group in the methacrylate group-modified hyaluronic acid of the step S1 has a degree of substitution of 25-35%.

It should be understood that the degree of substitution of the methacrylate group refers to a ratio of the peak area of methyl H in the methacrylate group to the peak area of methyl H on the side chain of hexose ring of the hyaluronic acid in the nuclear magnetic resonance (NMR) spectrum of the methacrylate group-modified hyaluronic acid.

Preferably, in the step S1, the methacrylate group-modified hyaluronic acid is prepared by the following method: dissolving hyaluronic acid or a salt thereof into water, adding a methacrylic anhydride first, and regulating a pH value to 8.45-8.55, performing a reaction for 20-24 and dialysis, to obtain the methacrylate group-modified hyaluronic acid.

More preferably, the reaction is performed at 35-40° C.

More preferably, the hyaluronic acid has a relative molecular weight of 90-100 kDa.

More preferably, a usage ratio of the hyaluronic acid to the methacrylic anhydride is 1 g:(2.8-3.2 mL).

More preferably, a dialysis bag for the dialysis has a size of 3000-5000 Da.

Preferably, the step S1 has the following specific process: dissolving the methacrylate group-modified hyaluronic acid into a morpholino-ethanesulfonic acid buffer solution first, adding 4-(4,6-dimethoxy-1,3,5-triazin-2-yl)-4-methylmorpholinium chloride, and adding furfuryl amine, mixing and reacting for 20-24 h, and conducting dialysis, to obtain the furan-methacrylate modified hyaluronic acid.

Preferably, in the step S1, the reaction has a temperature of 25-30° C.

More preferably, the morpholino-ethanesulfonic acid buffer solution has a pH value of 4.4-4.6.

More preferably, a mass ratio of the methacrylate group-modified hyaluronic acid to 4-(4,6-dimethoxy-1,3,5-triazin-2-yl)-4-methylmorpholinium chloride is 1:(2.8-3.0).

More preferably, a usage ratio of the methacrylate group-modified hyaluronic acid to furfuryl amine is 1 g:(0.35-0.40 mL).

More preferably, a dialysis bag for the dialysis has a size of 3000-5000 Da.

Preferably, the furan group in the furan-methacrylate modified hyaluronic acid of the step S1 has a degree of substitution of 55-65%.

It should be understood that the degree of substitution of the furan group refers to a ratio of the sum of peak areas of the three H atoms in the furyl five-carbon ring to the peak area of methyl H on the side chain of hexose ring of the hyaluronic acid in the NMR spectrum of the furan-methacrylate modified hyaluronic acid.

Preferably, the step S2 has the following specific process: dissolving the furan-methacrylate modified hyaluronic acid into water first, adding maleimide and mixing, conducting reacting for 20-24 h and dialysis, to obtain the hyaluronic acid modified with dual groups.

Preferably, in the step S2, the reaction has a temperature of 25-30° C.

More preferably, a mass ratio of the furan-methacrylate modified hyaluronic acid to maleimide is 1:(1.0-1.2).

More preferably, a dialysis bag for the dialysis has a size of 3000-5000 Da.

Preferably, in the component A of the step S3, the hyaluronic acid modified with dual groups has a concentration (mass/volume ratio) of 20 mg/mL-25 mg/mL.

Preferably, in the component A of the step S3, a mass ratio of the hyaluronic acid modified with dual groups to the photoinitiator is 1:(0.1-0.25).

Preferably, in the step S3, the photoinitiator is lithium phenyl-2,4,6-trimethylbenzoylphosphinate.

Preferably, in the step S3, the solvent is water, normal saline (NB), or a PBS buffer solution.

Preferably, the mercapto polyethylene glycol solution is a 4-arm mercapto polyethylene glycol solution.

Preferably, the mercapto polyethylene glycol solution has a concentration (mass/volume ratio) of 500-1500 mg/mL.

More preferably, the mercapto polyethylene glycol solution has a concentration (mass/volume ratio) of 500-1000 mg/mL.

Preferably, a volume ratio of the component A to the component B is 10:(1-2).

A preparation method of the above hyaluronic acid-based hydrogel precursor solution includes the following steps:

preparing the component A according to the preparation method of the component A, dissolving mercapto polyethylene glycol into a solvent to obtain the component B; mixing the component A with the component B before gelation.

A hyaluronic acid-based hydrogel is obtained after gelatinizing the above hyaluronic acid-based hydrogel precursor solution or hyaluronic acid-based hydrogel.

The hyaluronic acid-based hydrogel of the present invention may be either used in the form a precursor solution, or in the form of a gelatinized colloid.

Use of the above hyaluronic acid-based hydrogel in the preparation of a repair material for treating a maxillofacial combined injury also falls within the protection scope of the present invention.

Preferably, the repair material has a dosage form of dressing or spray; in addition to the above hyaluronic acid-based hydrogel precursor solution or hyaluronic acid-based hydrogel, the repair material further includes a growth factor, a preservative, etc.

Preferably, the repair material is a bone and/or skin defect repair material.

More preferably, the repair material is a bone and/or skin defect repair material for promoting the expression of ITGA6.

Preferably, the repair material is a repair material having a hemostatic function.

Compared with the prior art, the present invention has the following beneficial effects.

The hyaluronic acid-based hydrogel precursor solution of the present invention has a very high mobility, and can be injected and sprayed; the hyaluronic acid-based hydrogel precursor solution can achieve low self-healing, and fast self-healing under UV light irradiation. The hyaluronic acid-based hydrogel precursor solution of the present invention has a good hemostatic function, bone and skin defect repairing capabilities at the same time. Therefore, the hyaluronic acid-based hydrogel precursor solution of the present invention can provide an integrated therapeutic scheme for the combined injuries of maxillofacial soft and sclerous tissues, and thus has a good application prospect.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Figure 4:
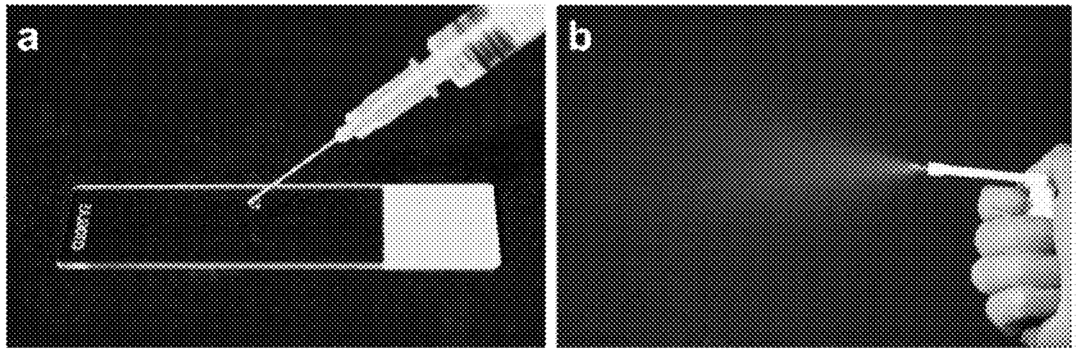

a of FIG. 4 is a schematic diagram showing injection use of the hyaluronic acid-based hydrogel precursor solution in Example 1; b of FIG. 4 is a schematic diagram showing spray use of the hyaluronic acid-based hydrogel precursor solution in Example 1.

Figure 5:
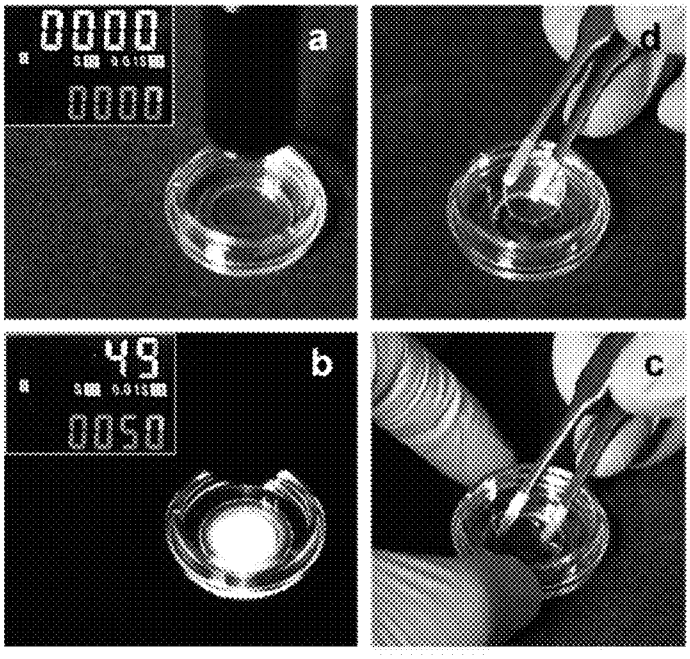

FIG. 5 is a schematic diagram showing a process of a gelation test under direct UV irradiation of the hyaluronic acid-based hydrogel precursor solution in Example 1.

Figure 6:
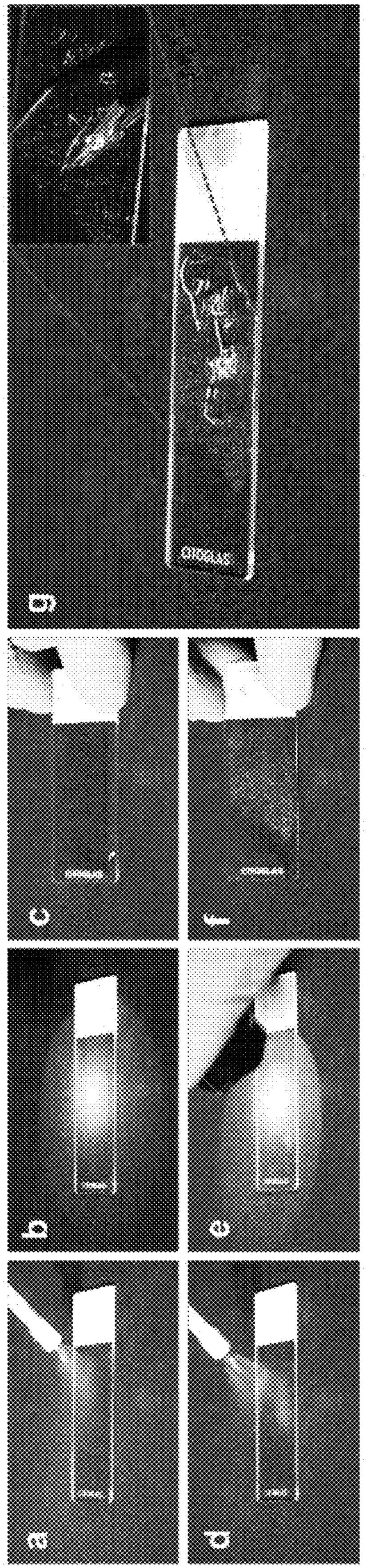

FIG. 6 is a schematic diagram showing a gelation process of the hyaluronic acid-based hydrogel precursor solution in Example 1 after being sprayed onto a slide.

Figure 7:
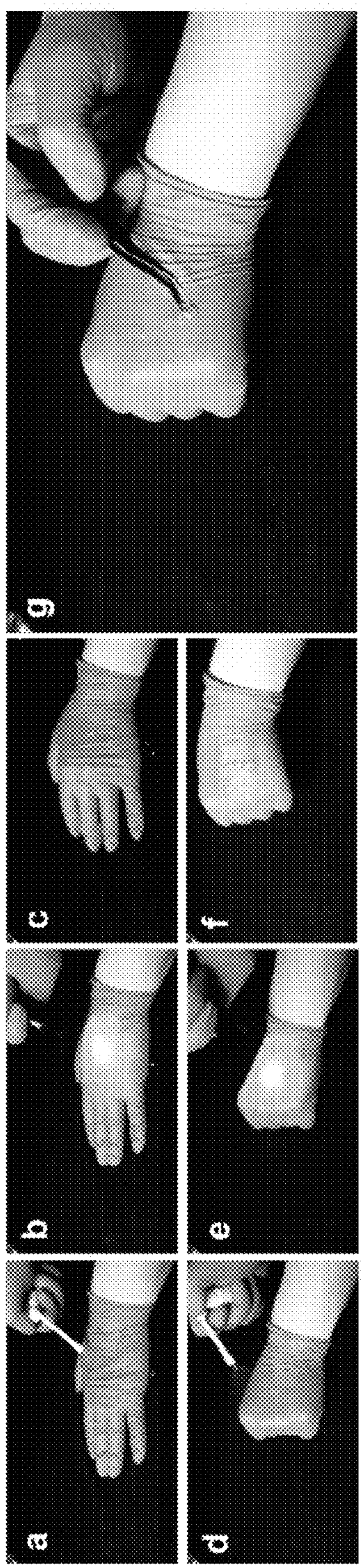

FIG. 7 is a schematic diagram showing a gelation process of the hyaluronic acid-based hydrogel precursor solution in Example 1 after being sprayed onto gloves.

Figure 8:
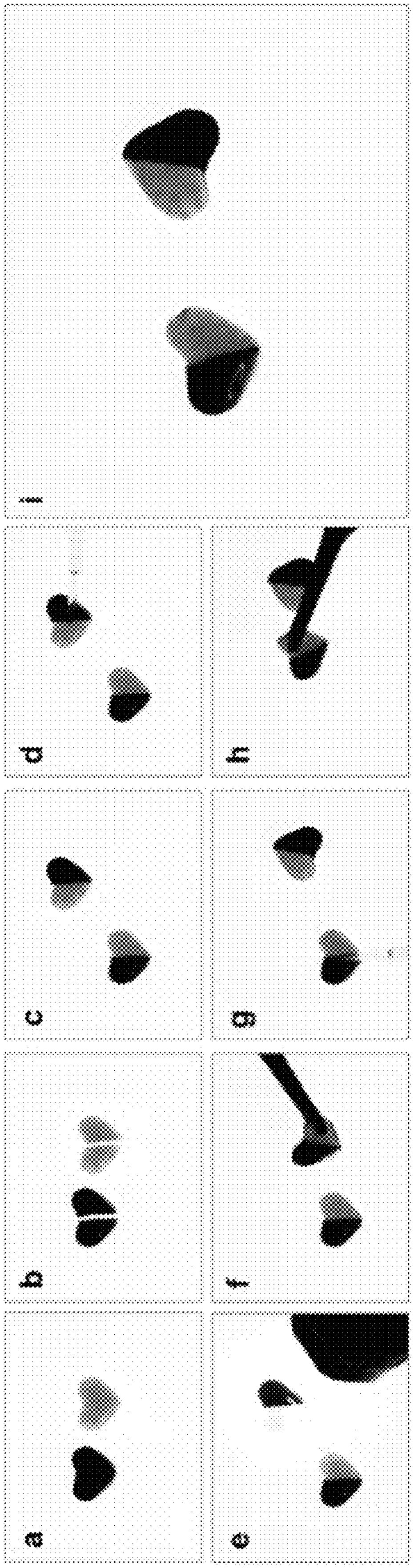

FIG. 8 is a schematic diagram showing processes of slow self-healing and rapid self-healing of the hyaluronic acid-based hydrogel precursor solution in Example 1, respectively.

Figure 9:
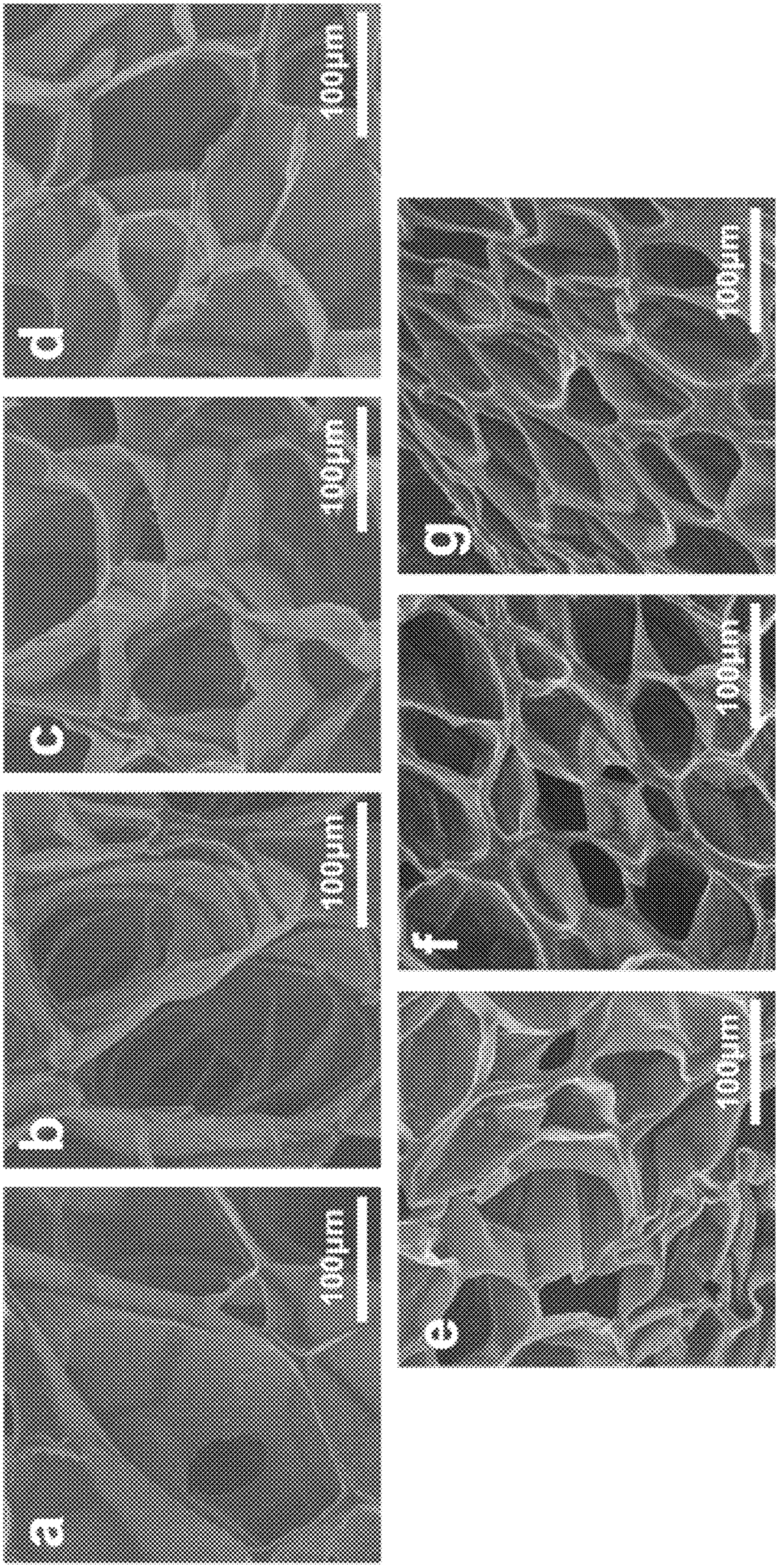

FIG. 9 shows a microstructure diagram of a hyaluronic acid-based hydrogel treated under different irradiation time after being frozen-dried.

Figure 10:
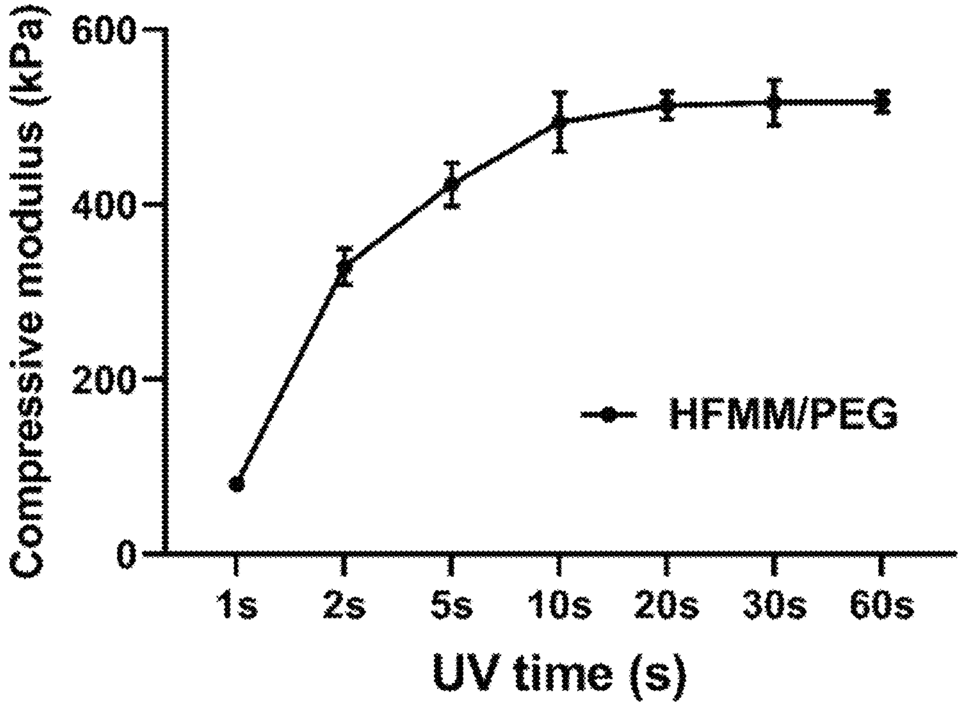

FIG. 10 shows a compressive modulus broken line graph of a hyaluronic acid-based hydrogel treated under different irradiation time.

Figure 11:
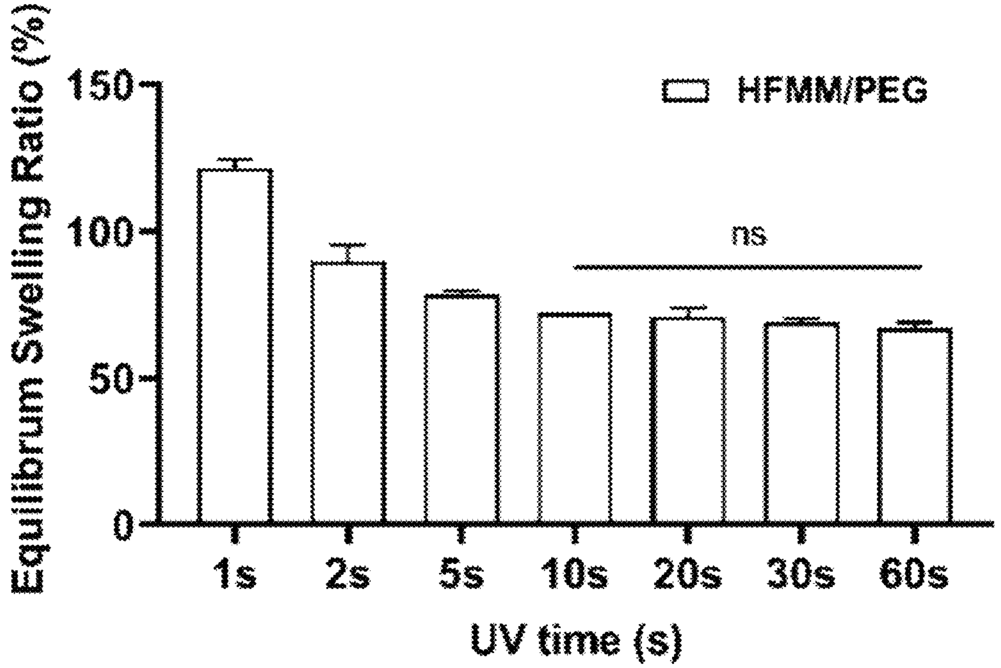

FIG. 11 shows equilibrium swelling ratios of a hyaluronic acid-based hydrogel treated under different irradiation time.

Figure 12:
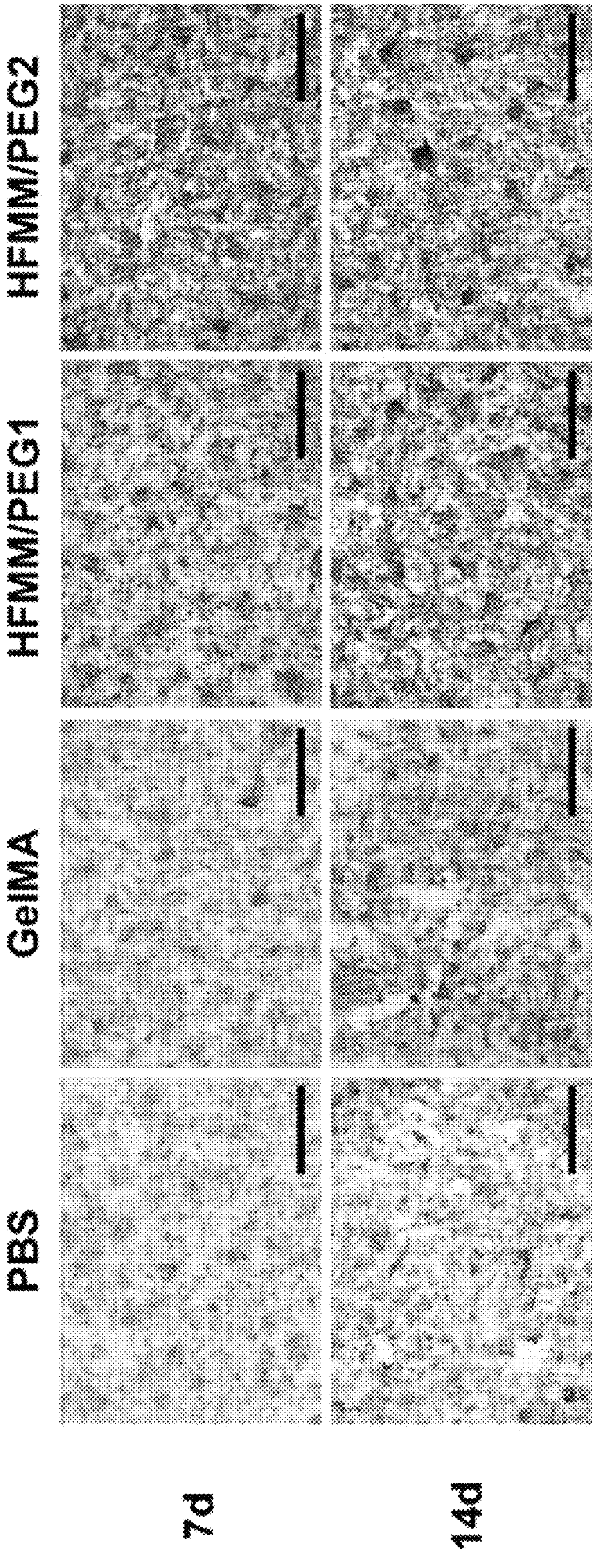

FIG. 12 is a diagram showing an experimental result of ALP staining in Example 5.

Figure 13:
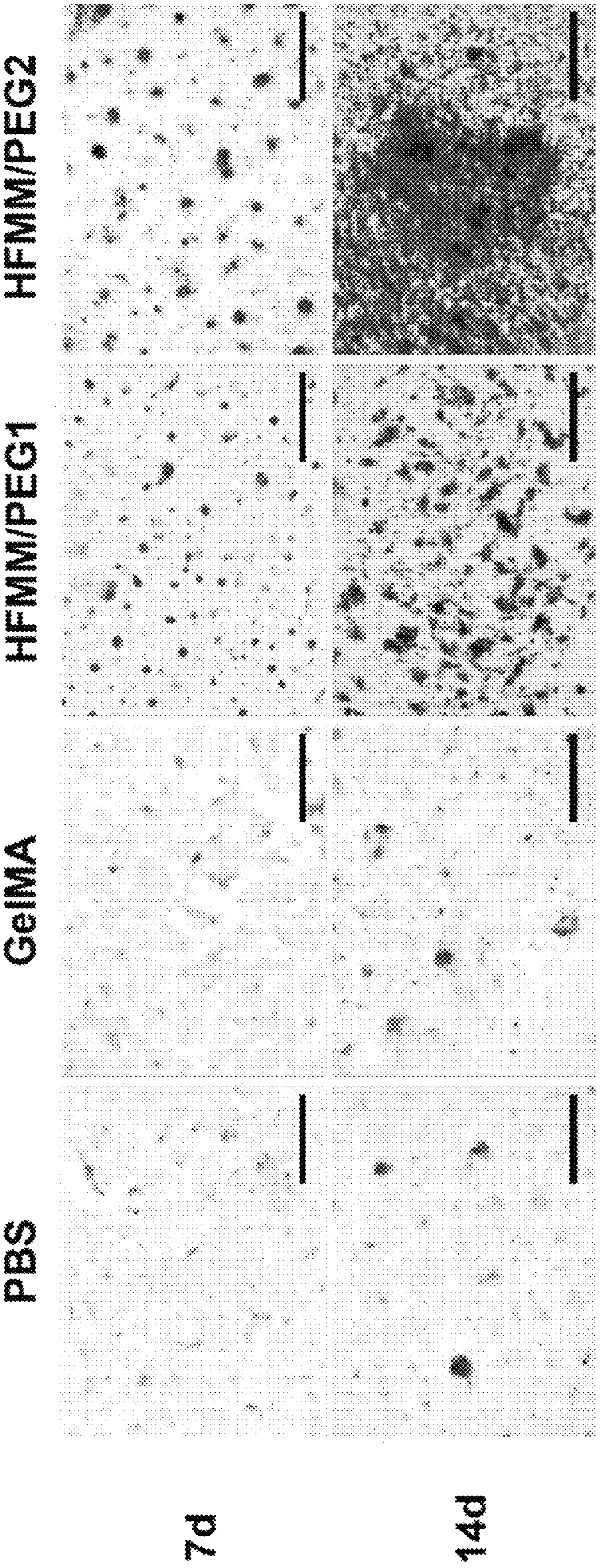

FIG. 13 is a diagram showing an experimental result of mineralization test via an alizarin red dye in Example 5.

Figure 14:
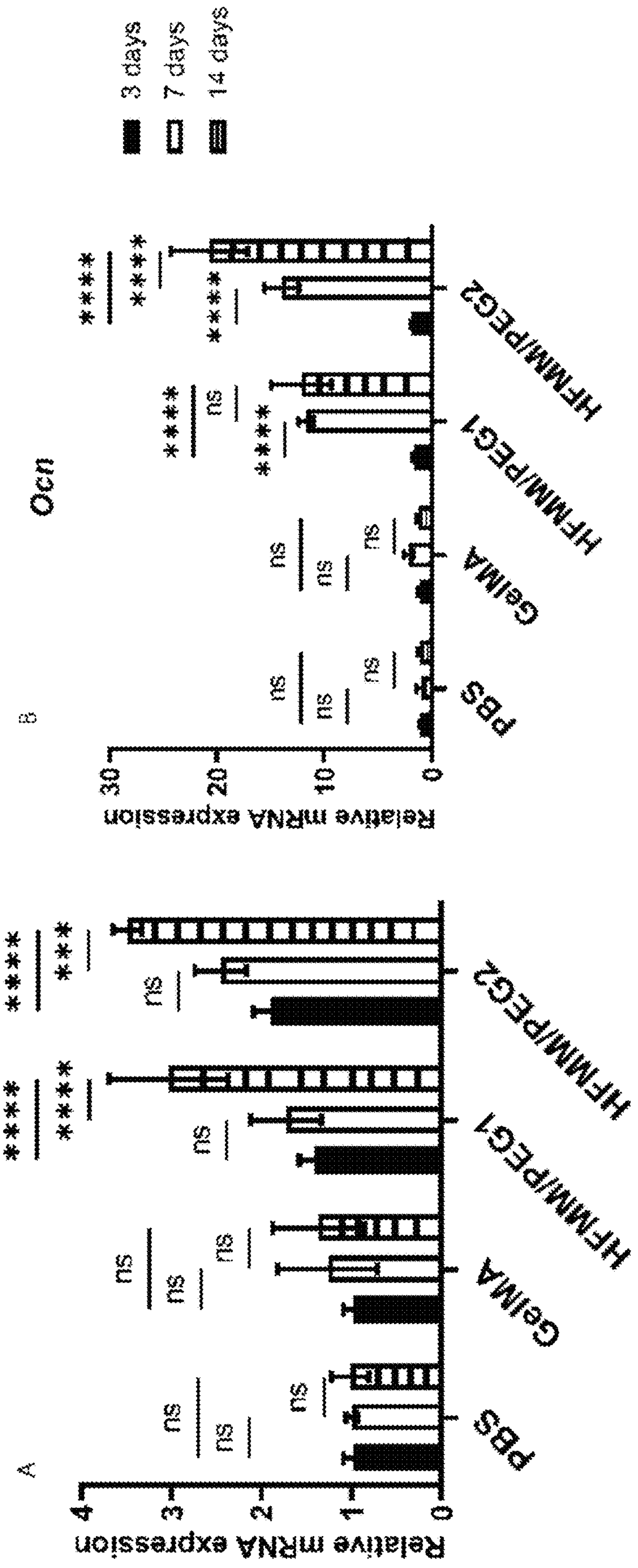

FIG. 14 is a diagram showing variations of rBMSCs transcriptional level in Example 5.

Figure 15:
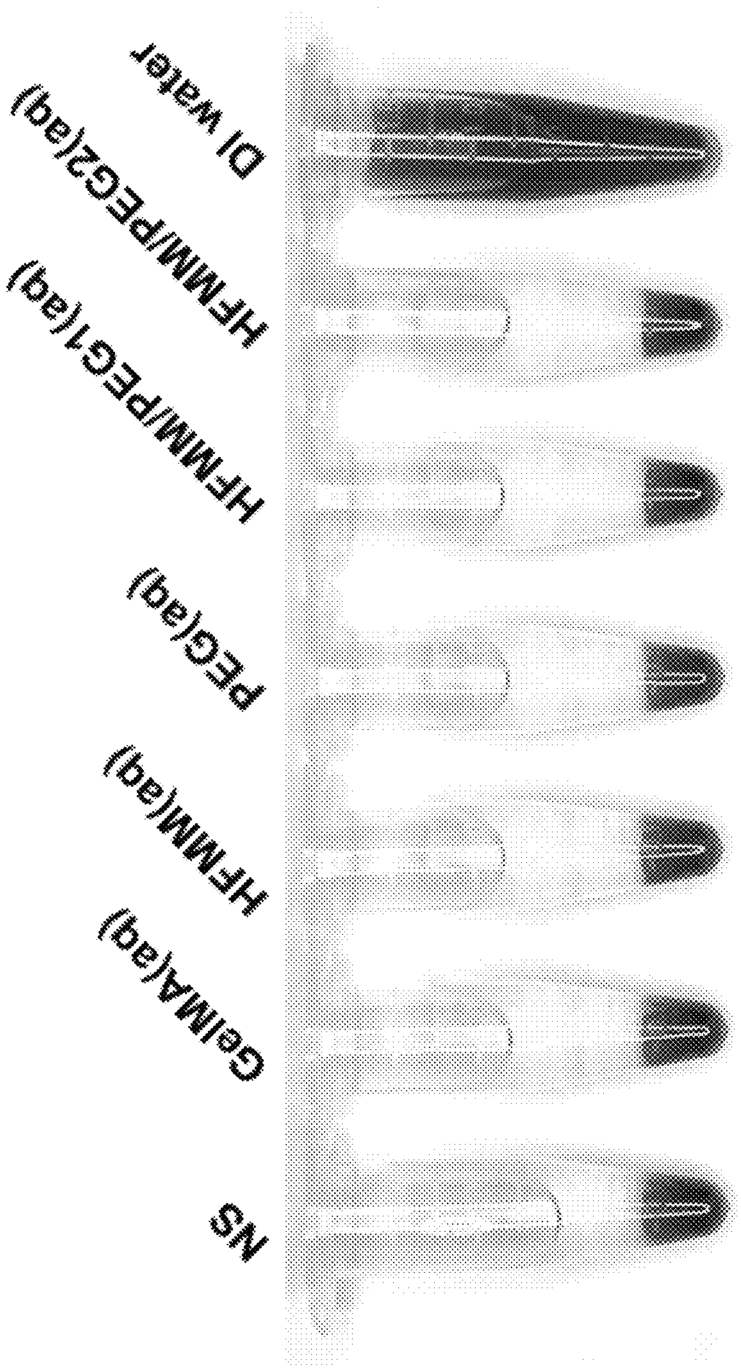

FIG. 15 is a diagram showing an experimental result of hemolytic property of a precursor solution in Example 6.

Figure 16:
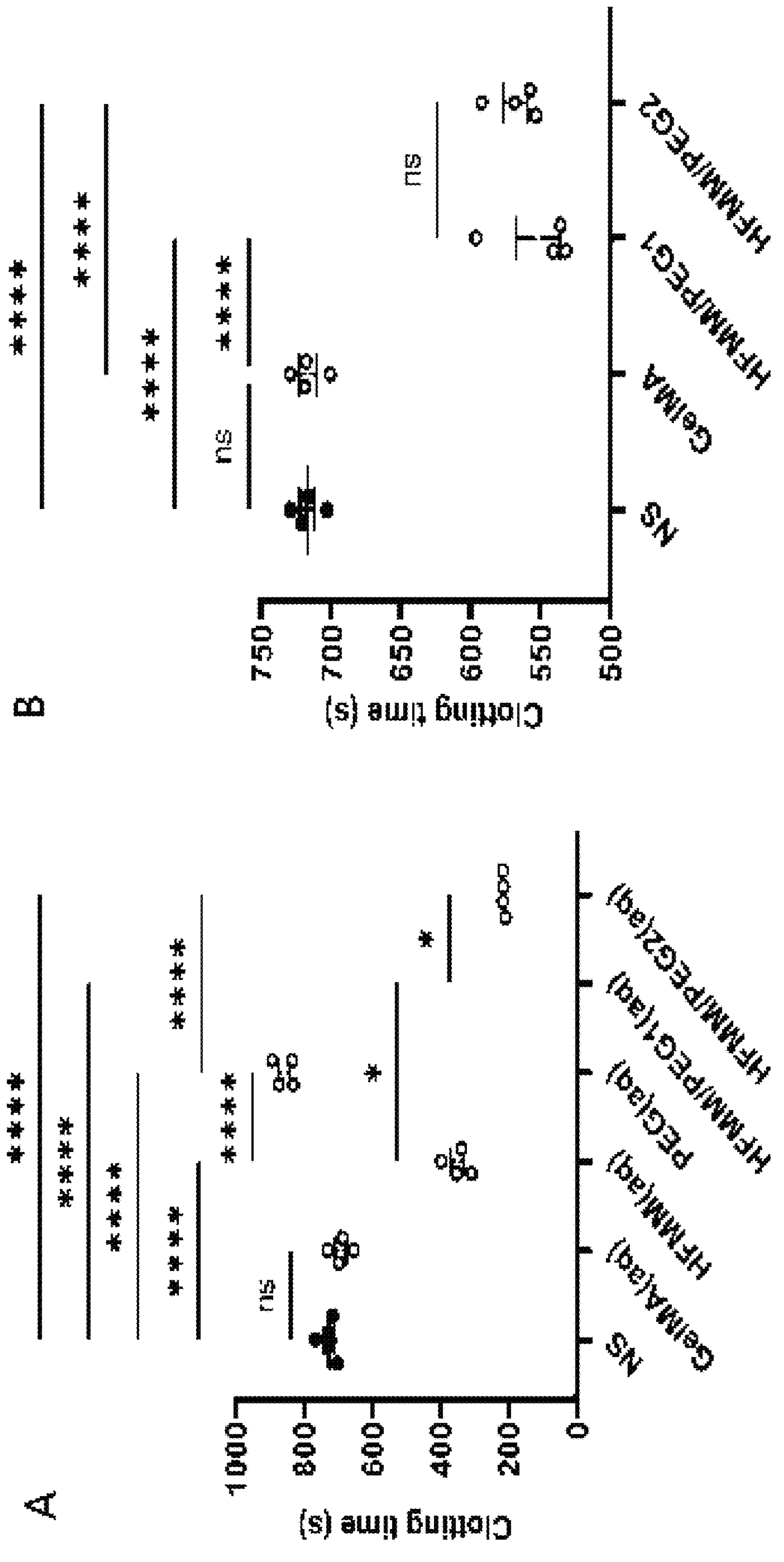

FIG. 16 is a diagram showing experimental data of ex vivo hemostasis of the precursor solution and hydrogel in Example 6.

Figure 17:
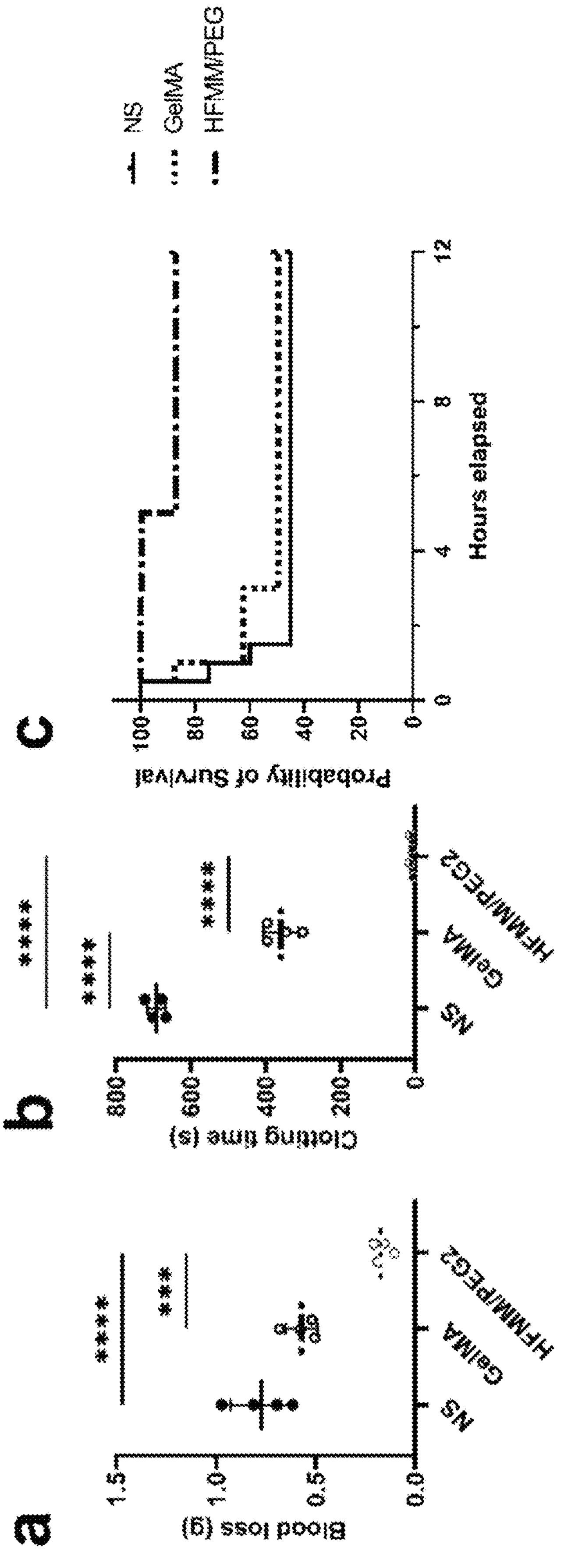

FIG. 17 is a diagram showing experimental data of the hemostasis experiment of a rat femoral venipuncture model in Example 6.

Figure 18:
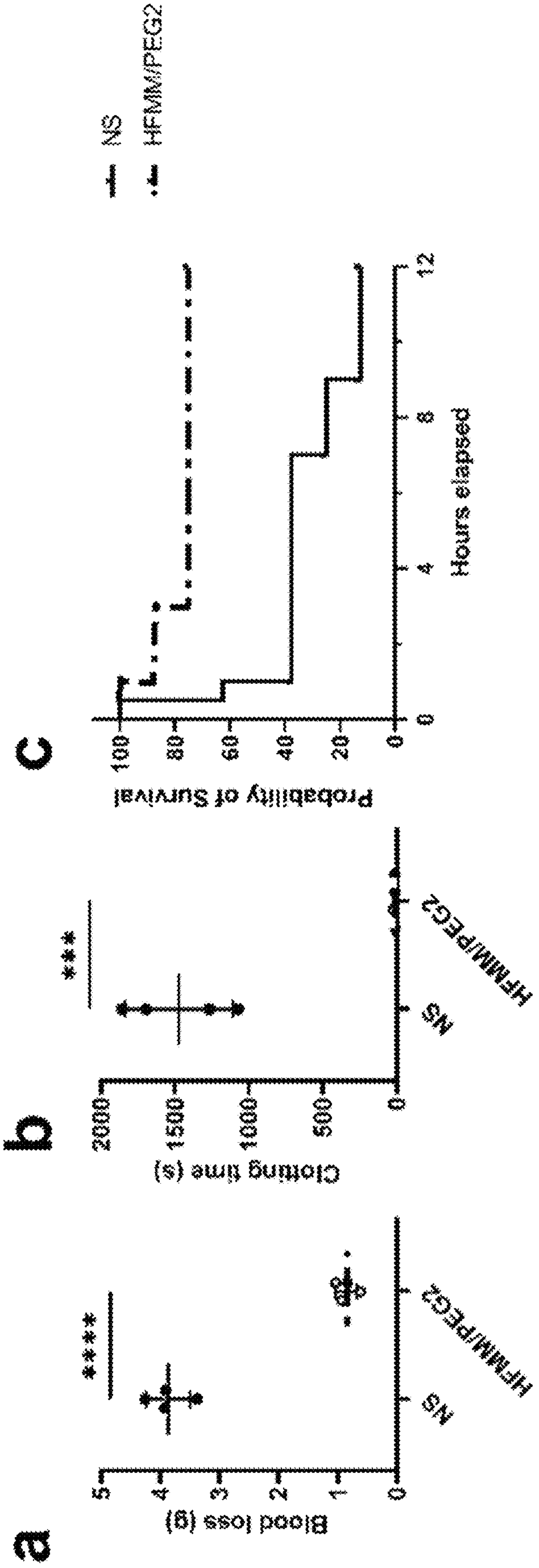

FIG. 18 is a diagram showing experimental data of the hemostasis experiment of a rat fatal liver injury model in Example 6.

Figure 19:
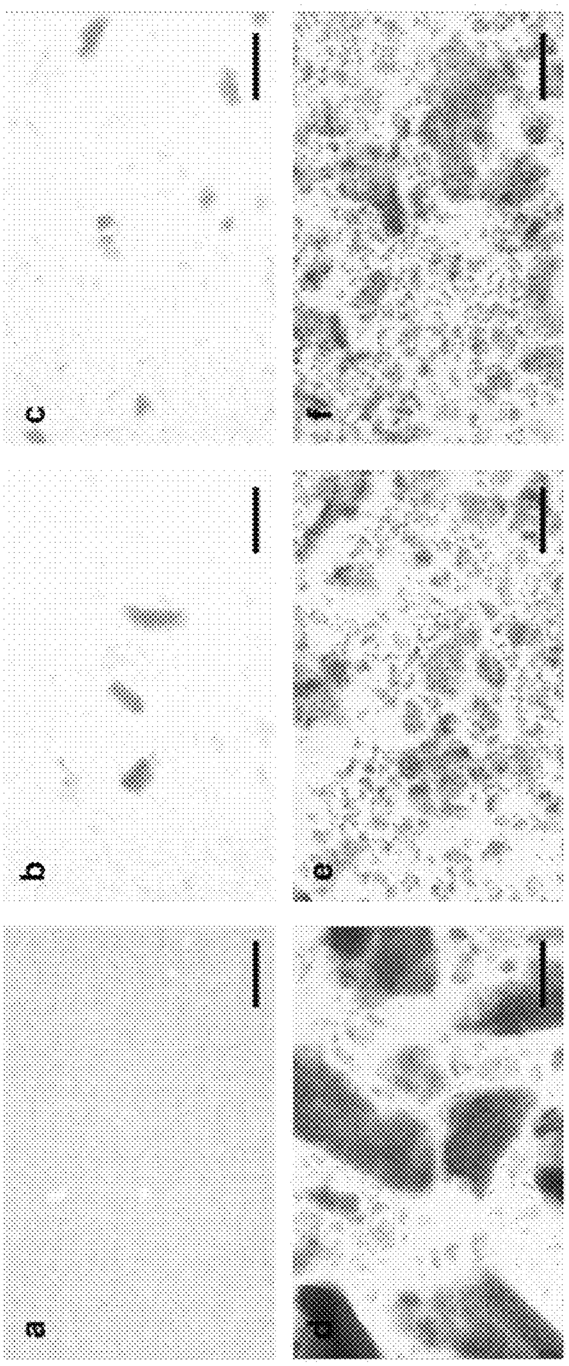

FIG. 19 is a diagram showing an experimental result of the hydrogel before gelation in erythrocyte aggregation analysis of Example 6.

Figure 20:
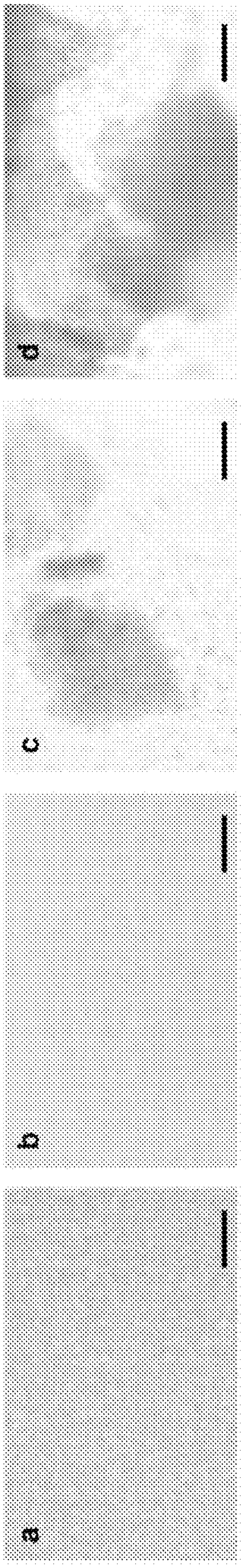

FIG. 20 is a diagram showing an experimental result of the hydrogel after gelation in erythrocyte aggregation analysis of Example 6.

Figure 21:
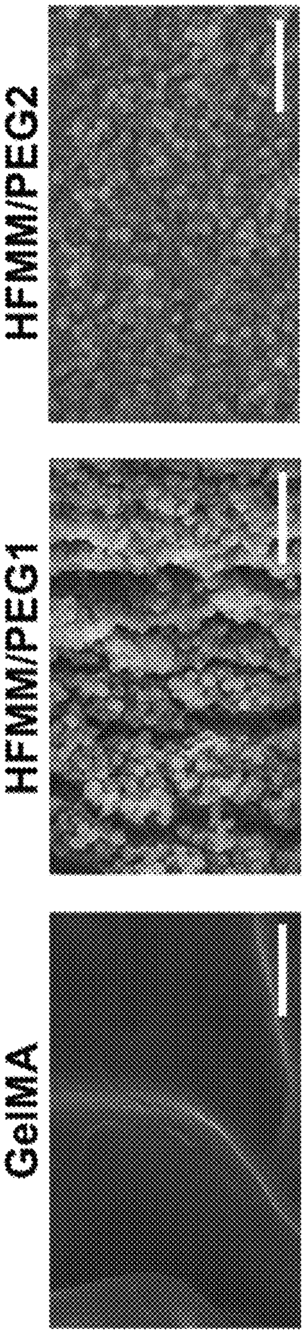

FIG. 21 shows scanning electron microscopy (SEM) graph of the erythrocyte aggregation analysis of Example 6.

Figure 22:
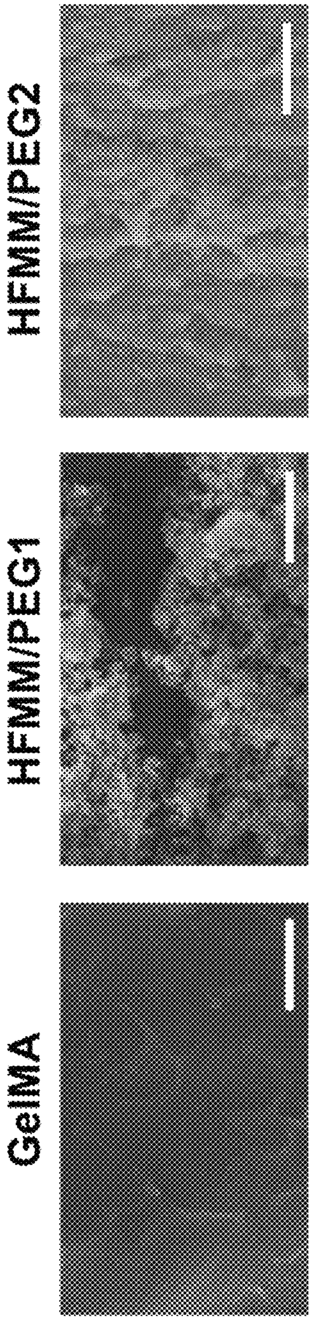

FIG. 22 shows an SEM graph of platelet aggregation analysis of Example 6.

Figure 23:
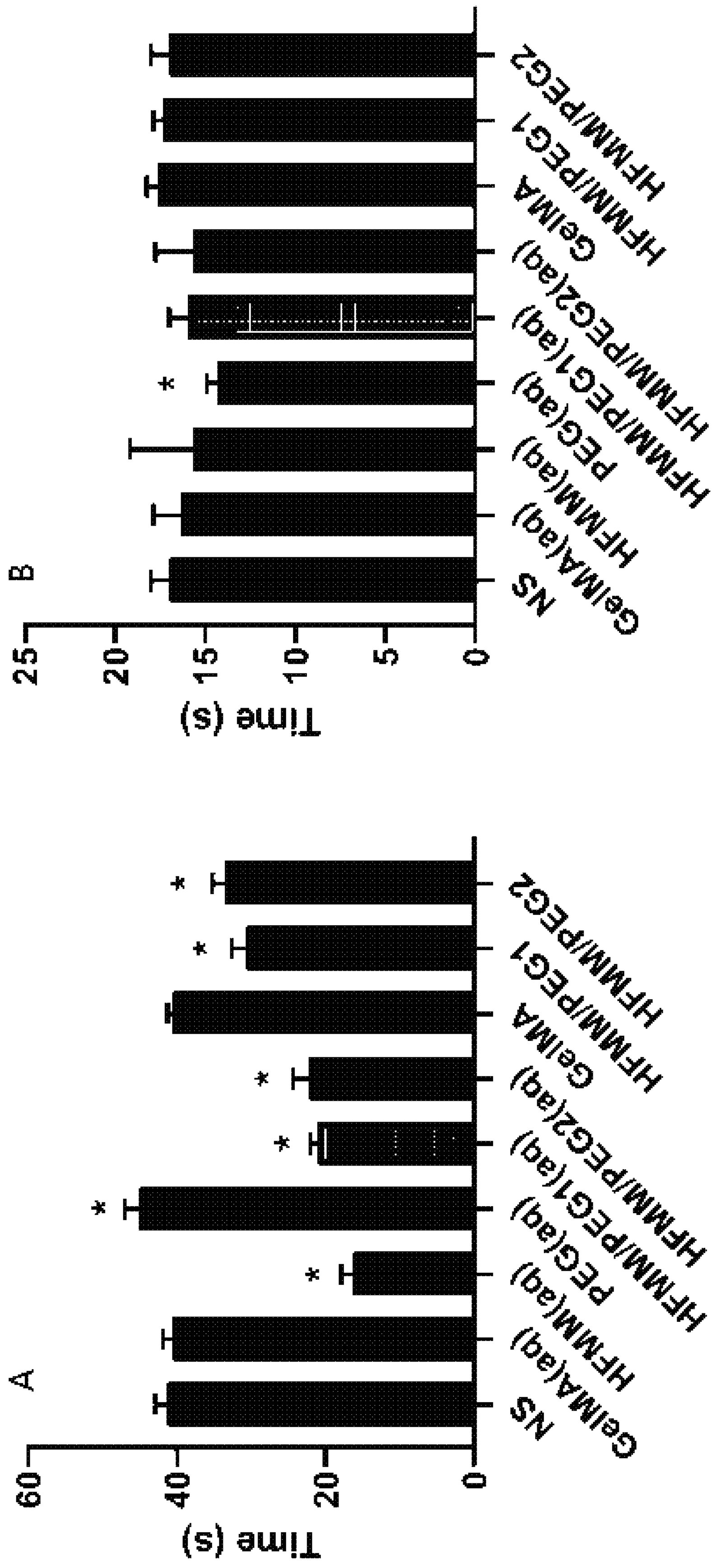

FIG. 23 is a diagram showing experimental data of a coagulation pathway activation in Example 6.

Figure 24:
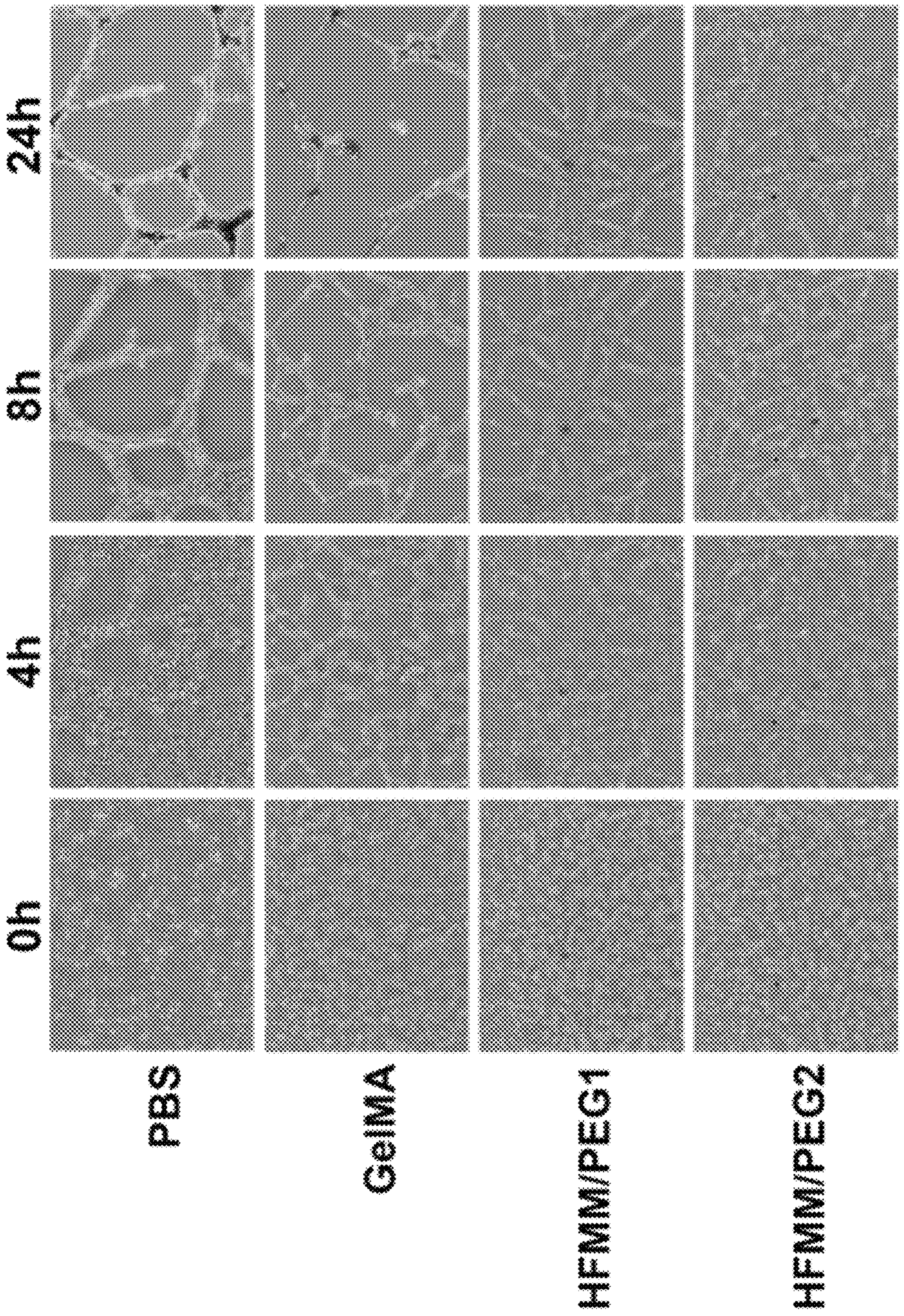

FIG. 24 is a diagram showing an experimental result of human umbilical vein endothelial cells (HUVEC) angiogenic capacity assessment in Example 7.

Figure 25:
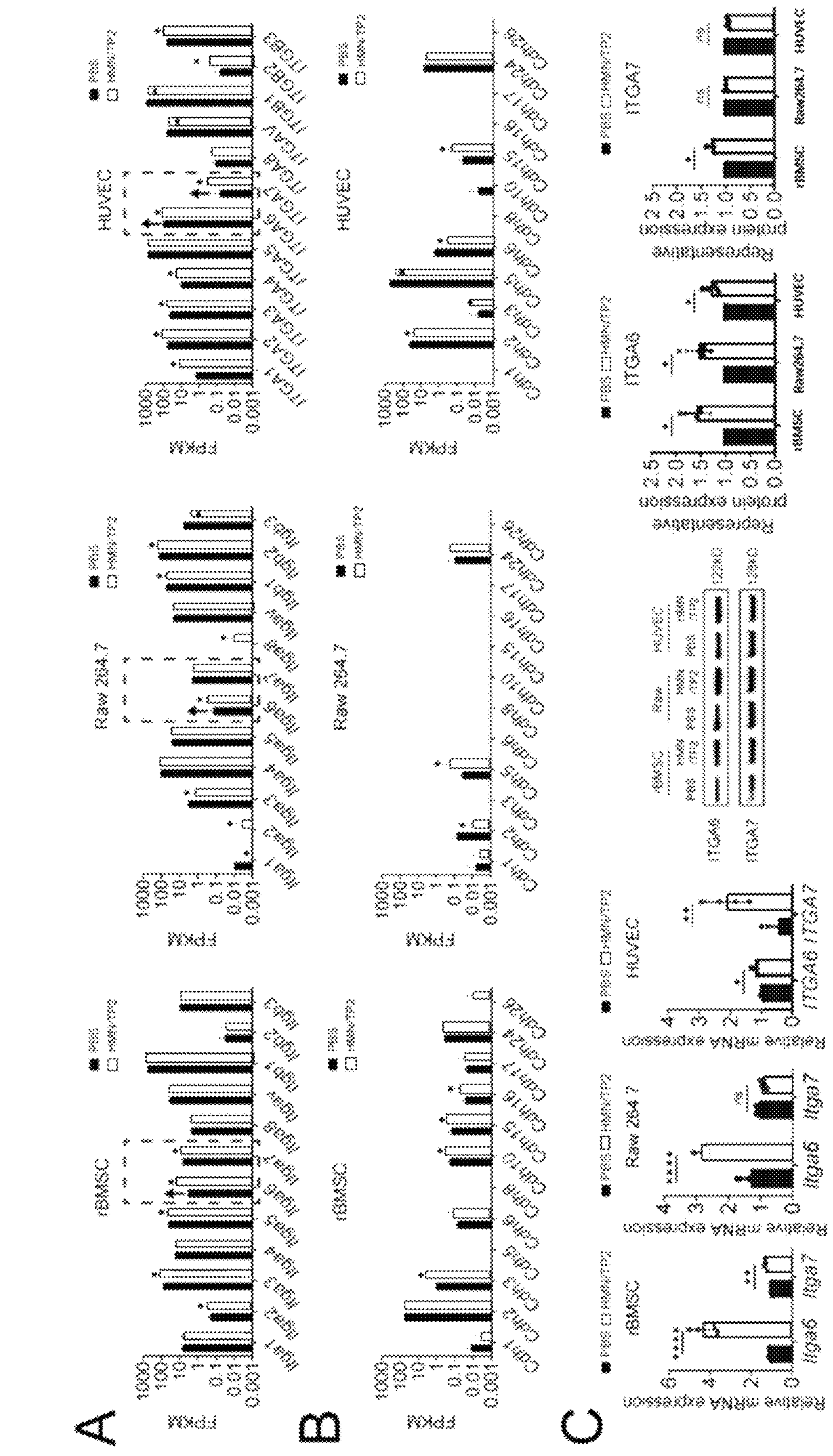

FIG. 25 is a diagram showing variation of adhesion protein or connexin genes after the hyaluronic acid-based hydrogel of Example 8 contacts the rBMSC, Raw264.7, and HUVEC cells.

Figure 26:
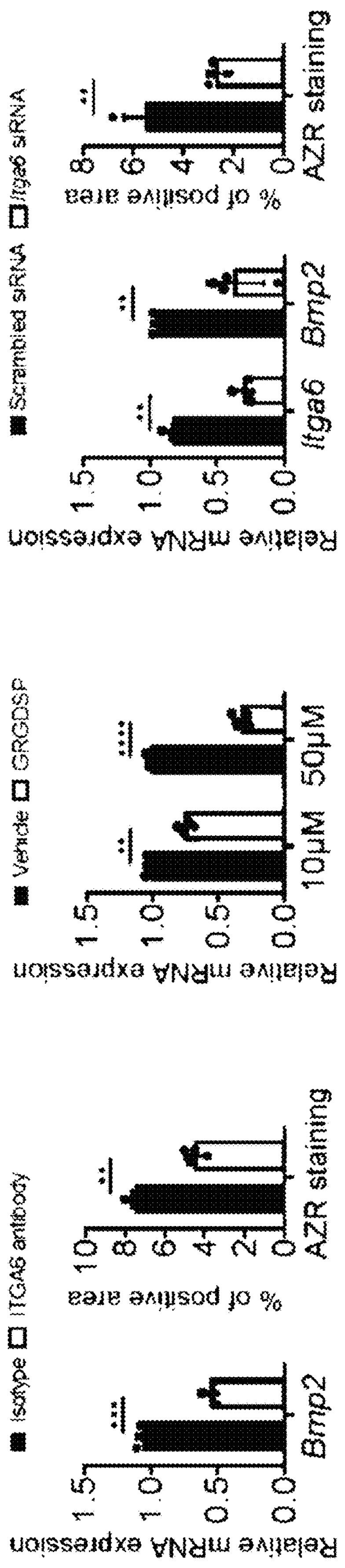

FIG. 26 is a diagram showing a result of variation of the osteogenic differentiation capacity of rBMSC in an experiment for inhibiting the expression of ITGA6 protein on cell surface in Example 8.

Figure 27:
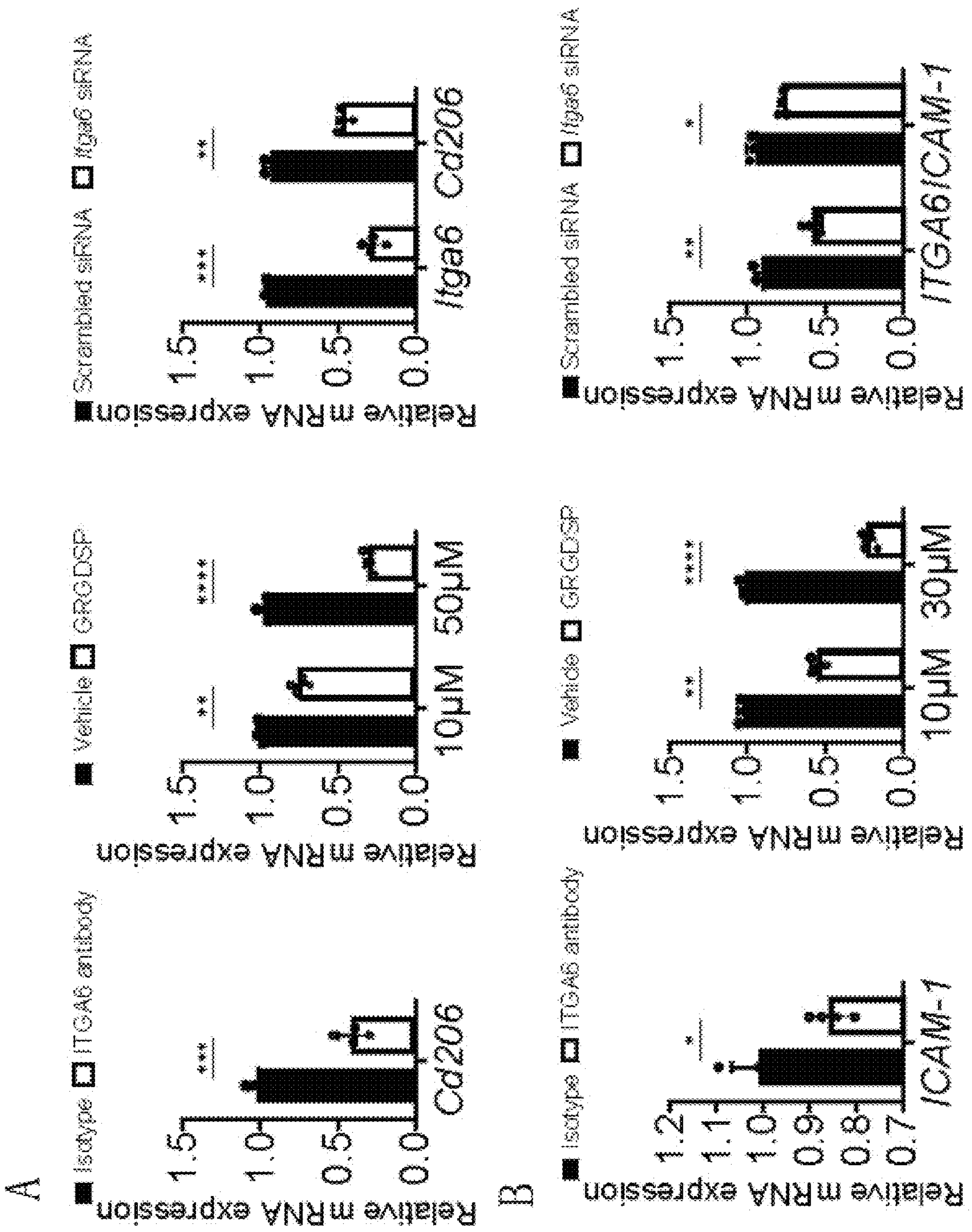

A of FIG. 27 shows variation results of the M2 differentiation capacity of Raw264.7 cells in an experiment for inhibiting the expression of ITGA6 protein on cell surface in Example 8; and B of FIG. 27 shows variation results of the angiogenic capacity of HUVEC in an experiment for inhibiting the expression of ITGA6 protein on cell surface in Example 8.

DESCRIPTION OF THE EMBODIMENTS

To describe the technical solutions of the present invention more clearly and completely, the present invention will be further specified in details by the following detailed embodiments. It should be understood that the detailed embodiments described below are merely for the interpretation of the present invention, but are not construed as limiting the present invention. Moreover, various variations of the detailed embodiments described below fall within the scope defined by the present invention.

Example 1

The example provides a hyaluronic acid-based hydrogel precursor solution; the hyaluronic acid-based hydrogel precursor solution includes a component A and a component B; the component A was prepared by the following steps:

1.1 Preparation of the Methacrylate Group-Modified Hyaluronic Acid 5 g solid sodium hyaluronate (denoted by HA, 100 kDa, Shanghai Yuanye Bio-Technology Co., Ltd.) was weighed and added to 500 mL deionized water, stirred at room temperature (25° C.) for 2 h until it was dissolved completely to colorless and transparent liquid; 15 mL methacrylic anhydride (MA, Sigma-Aldrich) was added dropwise and dripped off within 3 h; 5 M sodium hydroxide solution was used to regulate the pH value of the solution to 8.5, and the solution was then stirred for reaction overnight under a water bath at 37° C. The mixed solution after finishing the reaction was placed into a 3000 Da dialysis bag for dialysis, and exterior deionized water was replaced once every 8 h, lasting for 3 days. The obtained substance was collected and frozen-dried to a white flocculent solid, i.e., the methacrylate group-modified hyaluronic acid, denoted by HM.

1.2 Preparation of the Furan-Methacrylate Modified Hyaluronic Acid (100 mM, pH=4.5) morpholino-ethanesulfonic acid buffer solution (MES) was prepared first, and 1.2 L MES was taken and put to a 2 L brown beaker in the dark to be dissolved sufficiently; 4 g HM was then weighed and slowly added to MES at a magnetic stirring rate of 1000 rpm/min; the brown beaker was sealed with aluminum foil, and the solution was continuously stirred at room temperature for 2 h until HM was dissolved completely to form a clear and transparent solution.

11.2 g of 4-(4,6-dimethoxy-1,3,5-triazin-2-yl)-4-methylmorpholinium chloride (DMTMM) was weighed and slowly added to the preceding solution, and stirred for 1 h at room temperature; the carboxyl functional group on the backbone of hyaluronic acid was activated by DMTMM to obtain a mixed solution. 1.5 mL furfuryl amine (Furan, AR, Sigma-Aldrich) was added dropwise to the above mixed solution within 5 min, and sealed with aluminum foil, and continuously stirred at room temperature for 24 h.

The mixed solution after finishing the reaction was placed into a 3000 Da dialysis bag for dialysis, and exterior deionized water was replaced once every 8 h, lasting for 3 days, collected and frozen-dried to white flocculent solid, i.e., the furan-methacrylate modified hyaluronic acid, denoted by HFM.

1.3 Preparation of the Hyaluronic Acid Modified with Dual Groups 3 g frozen-dried HFM was weighed and added to 1.2 L deionized water, stirred at room temperature for 2 h until dissolved completely into colorless and transparent liquid; 3 g maleimide (Mal, AR, Sigma-Aldrich) was then added and stirred at room temperature for 1 day. The mixed solution after finishing the reaction was placed into a 3000 Da dialysis bag for dialysis, and exterior deionized water was replaced once every 8 h, lasting for 3 days. The obtained substance was collected and frozen-dried to a white flocculent solid, i.e., the hyaluronic acid modified with dual groups, denoted by HFMM.

1.4 Preparation of the Component A 0.4 g HFMM and 0.1 g of a photoinitiator, lithium phenyl-2,4,6-trimethylbenzoylphosphinate (LAP) were weighed and added to 20 mL deionized water, fully stirred and mixed well, and prepared to a 2% (wt/v) HFMM solution, i.e., the component A.

Figure 1:
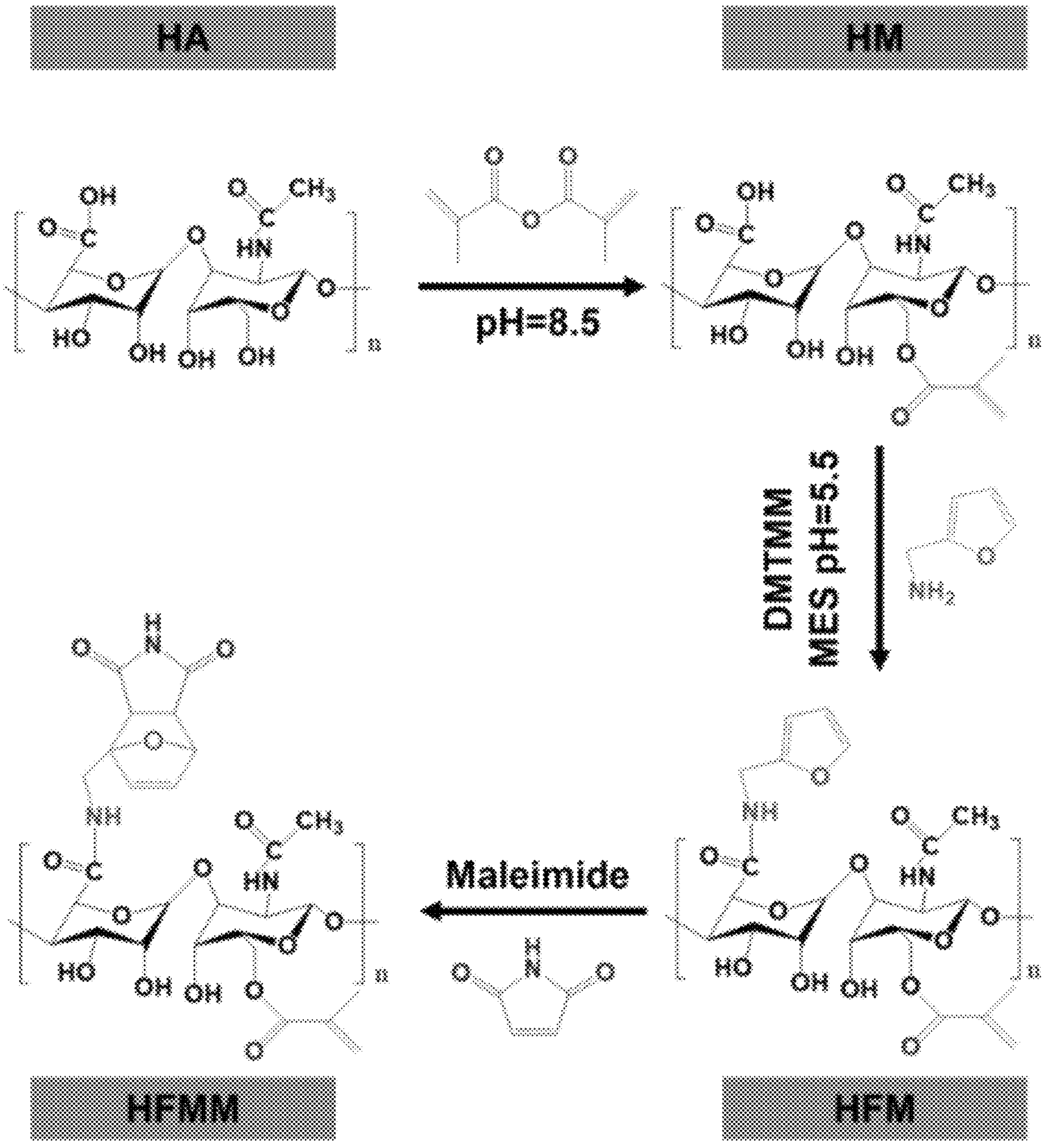
FIG. 1 is a schematic diagram showing a synthetic process of hyaluronic acid modified with dual groups in a component A of a hyaluronic acid-based hydrogel precursor solution in Example 1.

The schematic diagram of a synthetic process of the hyaluronic acid modified with dual groups is shown in FIG. 1.

In this example, the component B is an aqueous solution of 4-arm mercapto polyethylene glycol (PEG, 2 kDa. AR, Sigma-Aldrich) having a concentration of 500 mg/mL. When the hyaluronic acid-based hydrogel precursor solution of the present application was used, the component A was mixed with the component B in a volume ratio of 10:1, and gelatinized to obtain the hyaluronic acid-based hydrogel.

Example 2

The example provides a hyaluronic acid-based hydrogel precursor solution. Example 2 differs from Example 1 in that the component B is an aqueous solution of 4-arm mercapto polyethylene glycol (PEG, 2 kDa, AR, Sigma-Aldrich) having a concentration (wt/v) of 1000 mg/mL.

Example 3

The example provides a hyaluronic acid-based hydrogel precursor solution. Example 3 differs from Example 1 in that the component B is an aqueous solution of 4-arm mercapto polyethylene glycol (PEG, 2 kDa, AR, Sigma-Aldrich) having a concentration (wt/v) of 1500 mg/mL.

Example 4 Sample Characterization

In this example, each intermediate product and final product in Example 1 were taken for characterization.

4.1 Study on the Chemical Structure of Each Component

Figure 2:
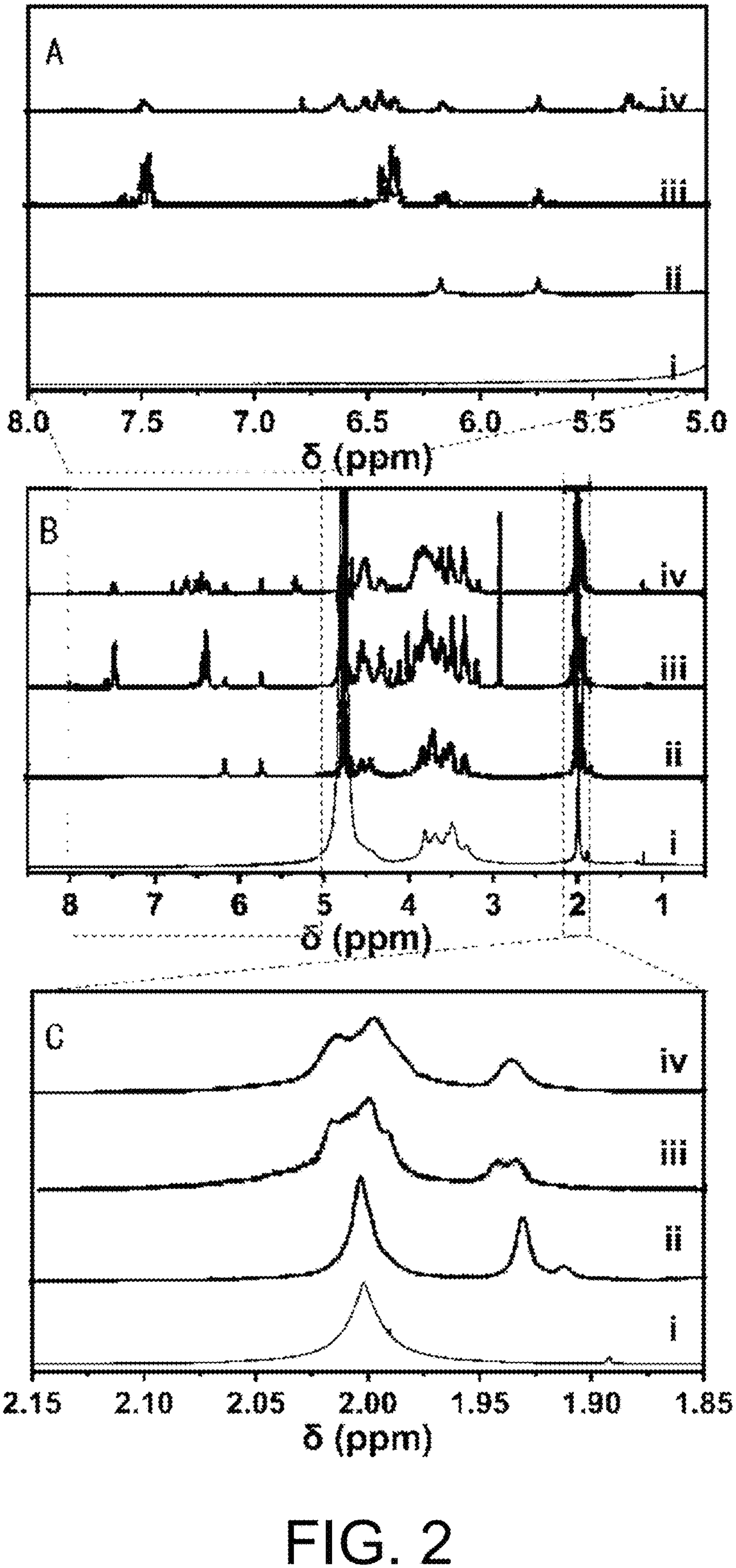
FIG. 2 shows NMR spectrum of intermediate products (HA, HM, and HFM) and a final product (HFMM) of Example 1.

HA, HM, HFM, and HFMM were weighed by 0.01 g, respectively, and dissolved into 0.5 mL $D_2O$, respectively until being dissolved completely. The mixed solution was then transferred to a clean NMR tube and subjected to HNMR test, respectively. Results are shown in FIG. 2. FIG. 2 shows an NMR spectrum (H-NMR, 600 MHz) of each component, where i represents HA; ii represents HM; iii represents HFM, and iv represents HFMM; where A and C of FIG. 2 show partial enlarged drawings of different chemical shift sections of B of FIG. 2, respectively.

As can be seen from FIG. 2,

HA's peak at a chemical shift of 2.00 ppm is the characteristic peak of methyl-H atom on the HA side chain. HM's double-bond characteristic peaks of the methacrylate group at 6.22 ppm and 5.75 ppm and the characteristic peak of methyl-H (from the methacrylate group) at 1.93 ppm are present, which proves that the hydroxyl of hydroxymethyl on the side chain of hexose ring of HA is subjected to grafting reaction with the methacrylic anhydride to form the HM. That is, the methacrylate group is smoothly grafted onto hyaluronic acid. Compared with other hydroxyl, the hydroxyl of the hydroxymethyl on the surface of hyaluronic acid is farthest away from the backbone of hyaluronic acid and has the smallest steric hindrance and thus, is subjected to esterification reaction with the methacrylate group most easily. The degree of substitution of the methacrylate group in HM refers to a ratio of the peak area (Area (1.93 ppm)) of methyl-H in the methacrylate group to the peak area (Area (2.00 ppm)) of methyl-H on the side chain of hexose ring of hyaluronic acid in the NMR spectrum of the methacrylate group-modified hyaluronic acid. The calculation formula is as follows:

$$DS = \frac{\text{Area (1.93 ppm)}}{\text{Area (200 ppm)}} \times 100\%.$$

By calculation, DS of the methacrylate group in HM is about 25%.

HFM retains the characteristic peak of methyl-H atom at 2.00 ppm, and methacrylate peaks at 6.22 ppm, 5.75 ppm, and 1.93 ppm, which indicates that the methacrylate group keeps stable in the modification process by furan. New characteristic peaks are present at chemical shifts of 6.35 ppm, 6.48 ppm, and 7.42 ppm, corresponding to three H atoms on the five-carbon ring of the furan group. It proves that the carboxy group on the side chain of hyaluronic acid molecule is subjected to amidation reaction with the amino group on the furfuryl amine molecule, and the furan group is smoothly grafted onto the HM. The degree of substitution of the furan group in HFM refers to a ratio of the sum of peak areas (Area (6.35 ppm)+Area (6.48 ppm)+Area (7.42 ppm)) of the three H atoms on the five-carbon ring of the furan group to the peak area (Area (2.00 ppm)) of methyl-H on the side chain of hexose ring of hyaluronic acid in the NMR spectrum of the furan-methacrylate modified hyaluronic acid. The calculation formula is as follows:

$$DS = \frac{\text{Area (6.35 ppm)} + \text{Area (6.48 ppm)} + \text{Area (7.42 ppm)}}{\text{Area (200 ppm)}} \times 100\%$$

By calculation, DS of the furan group in HFM is about 55%.

The HFMM similarly retains the characteristic peak of methyl H at 2.00 ppm, the characteristic peaks of the furan group at 6.35 ppm, 6.48 ppm, and 7.42 ppm, as well as the methacrylate peaks at 6.22 ppm, 5.75 ppm, and 1.93 ppm. It proves that the link of the maleimide group does not affect the modified group on the preceding product. Compared with the spectrum of HFM, the intensity of the chemical shift corresponding to the characteristic H atoms on the furan group weakens obviously. Meanwhile, a new peak is present at 5.29 ppm. The new peak is a characteristic peak of a double bond on the norbornene-like group generated between maleimide and the furan group via a DA click chemistry reaction. It indicates that the norbornene-like group is smoothly modified onto the side chain of hyaluronic acid. The degree of substitution of the norbornene-like group is mainly affected by the degree of substitution of the furan group. The property and functional activity of a gel will be affected by the grafting of an active group or not, type and position of the grafted active group, in a gel molecule. The above NMR data indicates that in the hyaluronic acid modified with dual groups of the present invention, the side chain of the hyaluronic acid has two photocrosslinked groups, i.e., the norbornene-like group and the methacrylate group simultaneously.

Compared with the pure hyaluronic acid, HFMM side chain is grafted with two photocrosslinked groups. Different photocrosslinked groups have different steric-hinerance effects. In this case, different grafting orders may affect the success of grafting or not and the degree of substitution of the two groups, which may ultimately affect the properties and functional activities of the hydrogel. In the present invention, the steric hindrance of the norbornene-like group is obviously greater than the methacrylate group. Therefore, if norbornene-like group is grafted first under MES environment, the degree of substitution of norbornene-like group is guaranteed. However, its steric hindrance affects the contact between methacrylic anhydride and the hydroxyl group on the surface of hyaluronic acid, thus affecting the degree of substitution of the methacrylate group.

In addition, methacrylizated hyaluronic acid is grafted via the hydroxyl of the side chain, and the reaction itself is harder than the amidation of the carboxyl group. Therefore, DS of the methacrylate group in HM is lower than that of merely grafting a methacrylate group on the surface of gelatin. When furan is grafted on the HM, the methacrylate group have already existed and thus, there exists steric hindrance. Therefore, DS of the furan group in HFM is lower than the situation of merely grafting a furan group on the surface of hyaluronic acid. However, in the HFMM of the present invention, the DS is still higher than 50%.

Additionally, the HFMM solution was subjected to a UV absorption spectrum test. An absorption peak is present at 217 nm which is from the conjugated diene structure in the furan group of the norbornene-like group. An absorption peak is present at 213 nm which is from the conjugated structure in the carbonyl group of maleimide of the norbornene-like group.

Figure 3:
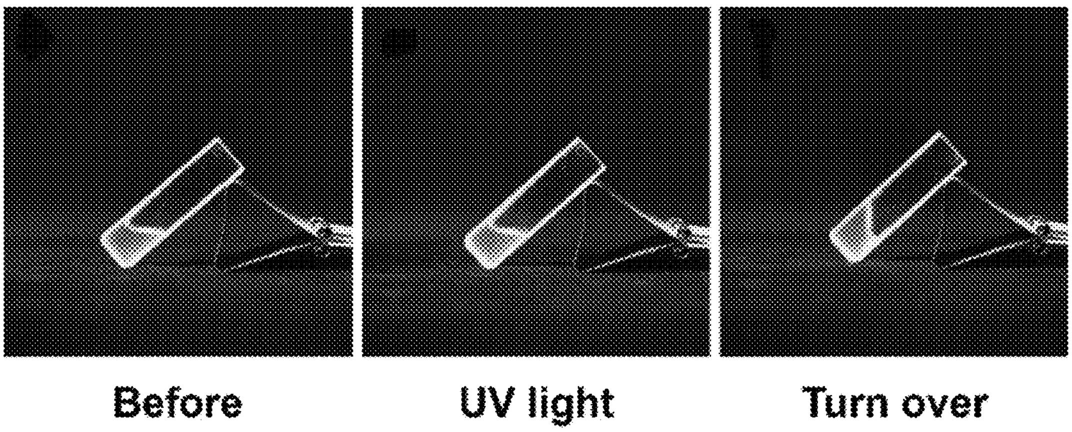
FIG. 3 is a schematic diagram showing a transformation process of the hyaluronic acid-based hydrogel precursor solution into a gel from a liquid state in Example 1.

4.2 Macro Morphology of the Hyaluronic Acid-Based Hydrogel a) The transformation of the hyaluronic acid-based hydrogel precursor solution into a gel from liquid state is achieved via transient UV irradiation, as shown in FIG. 3.

b) The component A was mixed with the component B, as shown in FIG. 4; the mixed solution may be not only injected (a of FIG. 4), but also may be sprayed (b of FIG. 4), indicating that the hyaluronic acid-based hydrogel precursor solution may have a high mobility and broad approaches to application. The hyaluronic acid-based hydrogel precursor solution of the present invention merely has a viscosity of 0.07 Pa-s at 1 Hz 10% shear strain (the shear strain test was conducted on a Malvern Kinexus rheometer, a parallel plate (P20 TiL, diameter of 40 mm) was used, 0.5 mL hydrogel precursor solution to be tested was dropwise added onto the plate; the plate spacing was 0.5 mm, test temperature was 25° C., stress was 10%, and frequency progressively increased from 0.01 Hz to 10 Hz for a total time of 60 s); it was only 2-4 times the viscosity of absolute ethyl alcohol (0.02-0.03 Pa-s). Therefore, the hyaluronic acid-based hydrogel precursor solution of the present invention may be sprayed before gelation.

c) FIG. 5 is a gelation test under direct UV irradiation. In FIG. 5, from 5a to 5b, the UV irradiation time was controlled by an electronic timer; the hyaluronic acid-based hydrogel precursor solution directly irradiated by UV light for 0.5 s; from 5b, 5c to 5d, the norbornene-like group and the methacrylate group in the hyaluronic acid modified with dual groups were subjected to rapid Thiol-ene photocrosslinking reaction with the mercapto group in 4-arm mercapto polyethylene glycol; gelation may be observed and the hydrogel slice may be intactly lifted. As can be seen from FIG. 5, the hyaluronic acid-based hydrogel precursor solution may be gelatinized only via 0.5 s of direct UV irradiation to the shortest. Compared with the hydrogel (10 s above in general) reported currently, the gelation rate is in the lead remarkably. Meanwhile, the hydrogel molded by rapid photocrosslinking after 0.5 s of direct UV irradiation is colorless and transparent. Moreover, the gelation test under direct UV irradiation further proves that the hyaluronic acid-based hydrogel precursor solution may be prepared, through a particular mold, to a shape corresponding to the mold size. It indicates that the hyaluronic acid-based hydrogel precursor solution may be used to sufficiently fill the tissue defect region, thus guaranteeing the regeneration and repair of the defect tissue.

d) The preceding test proves that the hyaluronic acid-based hydrogel precursor solution has a rapid gelation rate and high mobility and thus, may be sprayed onto the surface required to achieve rapid gelation after UV irradiation. Specifically, FIGS. 6 and 7 show the tests of the hyaluronic acid-based hydrogel precursor solution after being sprayed onto a slide and glove, respectively, where a-c of FIG. 6 and a-c of FIG. 7 are control groups sprayed with a PBS buffer solution; d-g of FIG. 6 and d-g of FIG. 7 are experimental groups sprayed with the hyaluronic acid-based hydrogel precursor solution; the hydrogel slices in g of FIG. 6 and g of FIG. 7 may be all lifted.

4.3 Self-Healing Performance of the Hyaluronic Acid-Based Hydrogel

The hyaluronic acid-based hydrogel precursor solution in Example 1 was taken. The hyaluronic acid-based hydrogel precursor solution may not only achieve rapid self-healing by means of a Thiol-ene rapid photocrosslinking reaction under UV irradiation, as shown in a-f of FIG. 8, but also may achieve slow self-healing by means of Michael chemical crosslinking, as shown in g-h of FIG. 8; the slow self-healing time is about 20 min. i of FIG. 8 shows an effect after finishing the self-healing, where the left represents the hydrogel for rapid self-healing, and the right one represents the hydrogel for slow self-healing.

4.4 Rheological Properties and Gelation Time of the Hyaluronic Acid-Based Hydrogel A rotational rheometer was used to detect the transformation process of the hyaluronic acid-based hydrogel into a gelatinous state after gelation from the liquid state of the precursor solution at a temperature of 25° C., a stress of 10%, a frequency of 1 Hz, lasting for 60 s. In case of no UV irradiation, cycling vibration stress was applied to the hyaluronic acid-based hydrogel precursor solution; the hyaluronic acid-based hydrogel precursor solution showed shear thinning, and the storage modulus (G') and loss modulus (G") declined to some extent at the same time. When a UV lamp (wavelength was 395 nm and power was 50 $mW/cm^2$) was used to irradiate from the space between the plate of the rheometer and the test stand (gap was about 0.5 mm), the hyaluronic acid-based hydrogel precursor solution is cured rapidly, showing the rapid increase of the storage modulus. The loss modulus also increases to a certain extent, but the increase range of the storage modulus is faster. Accordingly, when the storage modulus exceeds the loss modulus, the time point is the gelation point of the gel. As can be seen from the test (tested by a dynamic rheometer), the hyaluronic acid-based hydrogel has a gelation point of about 3.5 s, which further proves that the gelation rate of the hyaluronic acid-based hydrogel precursor solution in the present invention is obviously head of (for example, the gelation point of the GelMA hydrogel measured by the same method was about 27 s) the hydrogel reported at present.

4.5 Microstructure Change

FIG. 9 shows a microstructure diagram of a hyaluronic acid-based hydrogel treated under different irradiation time; from a-g of FIG. 9, the UV irradiation time is 1 s, 2 s, 5 s, 10 s, 20 s, 30 s, and 60 s, respectively; after the UV irradiation treatment, the product was taken out and frozen-dried to white flocculent solid, and then sliced, subjected to SEM. As can be seen from FIG. 9, when the irradiation time is 1-2 s, the frozen-dried hydrogel morphology network has a higher macroporous ratio, a lower microporous ratio, and a thinner wall of pore. With the increase of the irradiation time, the microporous ratio in the hydrogel network increases gradually; when the irradiation time exceeds 10 s, the porosity has minor change, and the increase rate of the degree of crosslinking reduces, indicating that the excessive UV irradiation has minor influence on the degree of crosslinking.

4.6 Mechanical Property

Mechanical compression resistance test of the hydrogel was conducted on a universal testing machine; the loading rate of the vertical compression stress was 1 mm/min, and the final stress of the load is 90%. FIG. 10 shows a compressive modulus broken line graph of a hyaluronic acid-based hydrogel treated under different irradiation time. As can be seen from FIG. 10, the compressive modulus of the hyaluronic acid-based hydrogel increases with the irradiation time; when the UV irradiation time is 1 s, the hyaluronic acid-based hydrogel has a compressive modulus of 80.18 kPa; when the UV irradiation time is 5 s, the hyaluronic acid-based hydrogel has a compressive modulus of 423.08 kPa, up to the 81.83% of the maximum compressive modulus. When the UV irradiation time is 10 s, the hyaluronic acid-based hydrogel has a compressive modulus being up to 90% of the maximum compressive modulus; when the UV irradiation time further increases, improvement in mechanical properties of the gel is not obvious. At the irradiation time of 60 s, the hyaluronic acid-based hydrogel of the present invention has a compressive modulus of being 400 kPa above, and being up to 517.02 kPa to the highest, which is much higher than the compressive modulus (about 80 kPa) of the GelMA hydrogel.

4.7 Swelling Property

The hyaluronic acid-based hydrogels irradiated by UV light were taken out one by one, and frozen-dried to white spongy solid, i.e., the frozen-dried hydrogel samples; and the original weight of the samples was denoted as $M_0$. The frozen-dried hydrogel sample was placed into a 6-well plate, and 5 mL deionized water was added to completely soak the frozen-dried hydrogel sample; the frozen-dried hydrogel sample was taken out every other a certain time t (t=1 h, 2 h, 4 h, 8 h, and 12 h); residual water on the surface of the sample was slightly blotted up by filter paper, and the sample was then weighed and denoted as Mt, the value of the Mt was denoted as the weight $M_{tmax}$ under equilibrium swelling until it no longer changed. Equilibrium swelling rate (ESR)=$(M_{tmax}-M_0)/M_0$.

FIG. 11 shows a swelling equilibrium water absorption result of a hyaluronic acid-based hydrogel treated under different irradiation time. As can be seen from FIG. 11, with the increase of the irradiation time, the hyaluronic acid-based hydrogel has gradually decreased ESR; when the irradiation time is 1 s, the hyaluronic acid-based hydrogel has the maximum ESR, being 121.6%; when the irradiation time is within 5 s, the ESR decreases most obviously; when the irradiation time exceeds 10 s, the descend range of the ESR reduces gradually; and when the irradiation time is 10 s, the hyaluronic acid-based hydrogel of an ESR of 69.2%. The above results indicate that the hyaluronic acid-based hydrogel of the present invention has very strong hydrophilicity, and has good water retention capacity as a matrix material.

The hyaluronic acid-based hydrogel precursor solution in Examples 2-3 has the performance similar to Example 1, and also may achieve rapid gelation and have high mobility, could be injected and sprayed, and have good self-healing capacity, mechanical properties and swelling properties.

Example 5 Bone Defect Repair Capacity of the Hyaluronic Acid-Based Hydrogel

Based on the hyaluronic acid-based hydrogel precursor solutions of Examples 1-2, in this example, deionized water in the component A was replaced into an equal volume of PBS, and then the component A was mixed with the component B for testing; the hyaluronic acid-based hydrogel precursor solutions of Examples 1-2 were denoted as HFMM/PEG1 hydrogel and HFMM/PEG2 hydrogel, respectively. In addition, 5% (wt/v) methylacryloylated gelatin hydrogel (denoted as GelMA, methylacryloylated gelatin was purchased from EFL-Tech Co., Ltd., Suzhou, China) served as a control group. UV irradiation time of each group was 10 s, and the UV-light wavelength was 395 nm, and power was 50 mW/cm$^2$.

5.1 Isolation and Purification of Rat rBMSCs

Healthy SPF-grade male SD rats (about 80 g in size) were narcotized, killed by cervical dislocation, and soaked into 75% ethanol. Skin was cut off on a bechtop; shin bone and thighbone were taken and subjected to bone marrow aspiration, and medullary space was washed off by a serum-free DMEM-F12 medium. rBMSCs were cultured on a 10% fetal calf serum (FBS)-containing DMEM-F12 by a whole bone marrow culture method; the double-antibody had a concentration of 50 IU/mL. The culture temperature was 37° C. The rBMSCs for the test were cells from generation 2 to generation 6.

5.2 Test on the Cell Viability and Cell Proliferation of the rBMSCs after being Co-Cultured with the Hydrogel The rBMSCs viability was detected by a CCK-8 kit. The rBMSCs in the culture flask were digested with a pancreatin, and inoculated onto a 48-well plate by 200,000/well, and cultured in a 10% FBS-containing DMEM-F12 for 24 h; the HFMM/PEG1 hydrogel and the HFMM/PEG2 hydrogel synthesized in advance (i.e., gelatinized after UV irradiation) were placed into the wells and co-cultured, respectively; the equal volume of PBS and GelMA were added to the control group, respectively. 24 h later after the co-culture, 30 μL CCK-8 test solution was added per well and continuously incubated for 3 h, then 100 μL supernatant was taken out per well and transferred into a 96-well plate; absorbance was detected at 450 nm.

The experimental results show that the cell viability of the PBS, GelMA, HFMM/PEG1 hydrogel, and HFMM/PEG2 hydrogel is greater than 100%, 24 h later after the co-culture, indicating that the hyaluronic acid-based hydrogel of the present invention is non-toxic.

The proliferation ability of rBMSCs was detected by a CCK-8 kit. The rBMSCs in the culture flask were digested with a pancreatin, and inoculated onto a 48-well plate by 100,000/well, and cultured in a 10% FBS-containing DMEM-F12 for 24 h; the HFMM/PEG1 hydrogel and the HFMM/PEG2 hydrogel synthesized in advance were placed into the wells and co-cultured, respectively; the equal volume of PBS and GelMA were added to the control group, respectively. 30 μL CCK-8 test solution was added per well at different time points of proliferation and continuously incubated for 3 h, then 100 μL supernatant was taken out per well and transferred into a 96-well plate; absorbance was detected at 450 nm.

The experimental results show that 3 d later after the co-culture, the rBMSCs have good proliferative activity at the HFMM/PEG1 hydrogel and HFMM/PEG2 hydrogel co-culture systems; the cell multiplication rate is 1.10 and 1.12 times the PBS group, respectively; the GelMA may not accelerate the proliferation of rBMSCs itself. It indicates that the hyaluronic acid-based hydrogel of the present invention has certain acceleration effect on the proliferation of rBMSCs.

5.3 Test on the Alkaline Phosphatase (ALP) Activity, ALP Staining and Mineralization of the rBMSCs after being Co-Cultured with the Hydrogel The ALP expression quantity was detected by an ALP kit, and a BCA protein quantification kit. The rBMSCs in the culture flask were digested with a pancreatin, and inoculated onto a 48-well plate by 100,000/well, and cultured in a 10% FBS-containing DMEM-F12 for 24 h; the HFMM/PEG1 hydrogel and the HFMM/PEG2 hydrogel synthesized in advance were placed into the wells and co-cultured, respectively; the equal volume of PBS and GelMA were added to the control group, respectively. The cells were lysed by 0.1% Trition-100 at different time points, 100 μL lysis solution was taken per well and added to a 96-well plate, and an ALP kit was used to detect ALP absorbance. 25 μL lysis solution was taken per well and transferred into a 96-well plate, and subjected to BCA protein quantification. Finally, the ALP absorbance value per well was normalized according to the BCA test result.

The experimental results show that the PBS group has the lowest ALP activity, being 0.17 μg/L at the 7th day. The group GelMA and the group PBS had no statistical significance in the difference of the ALP activity. The HFMM/PEG1 hydrogel and HFMM/PEG2 hydrogel co-culture systems have much higher relative activity, being 1.44 and 1.61 times the PBS group.

The group GelMA and the group PBS had no statistical significance in the difference of the cell ALP activity on the 14th day. The remaining groups had obvious difference in ALP activity; the ALP activity of the HFMM/PEG1 hydrogel and HFMM/PEG2 hydrogel is 2.59 and 2.96 times the PBS group. The above results indicate that the hyaluronic acid-based hydrogel of the present invention may accelerate the osteogenic differentiation of rBMSCs.

A Beyotime ALP staining kit was used for ALP staining. The rBMSCs in the culture flask were digested with a pancreatin, and inoculated onto a 6-well plate by 500,000/well, and cultured in a 10% FBS-containing DMEM-F12 for 24 h; the HFMM/PEG1 hydrogel and the HFMM/PEG2 hydrogel synthesized in advance were placed into the wells and co-cultured, respectively; the equal volume of PBS and GelMA were added to the control group, respectively. The cells were immobilized by paraformaldehyde for 15 min at different time points, washed with PBS for 3 times; 2 mL ALP staining working solution was added per well for incubation for 30 min at room temperature. After being washed for 5 times with PBS, the cells were placed under a stereo microscope for observation.

The experimental results are shown in FIG. 12. The blue deep-dyeable regions of the HFMM/PEG1 hydrogel and the HFMM/PEG2 hydrogel are obviously more than those of the groups GelMA and PBS at the same culture time. On the 14th day, the calcified areas of the rBMSCs in the HFMM/PEG1 and HFMM/PEG2 groups appeared in blocks, while the calcified areas in the groups GelMA and PBS appeared sporadically.

Mineralization was detected via an alizarin red dye. The rBMSCs in the culture flask were digested with a pancreatin, and inoculated onto a 6-well plate by 500,000/well, and cultured in a 10% FBS-containing DMEM-F12 for 24 h; the HFMM/PEG1 hydrogel and the HFMM/PEG2 hydrogel synthesized in advance were placed into the wells and co-cultured, respectively; the equal volume of PBS and GelMA were added to the control group, respectively. The cells were immobilized by paraformaldehyde for 15 min at different time points, washed with PBS for 3 times; 2 mL alizarin red S (2% w/v) solution was added per well for incubation for 30 min at room temperature. After being washed for 5 times with PBS, the cells were placed under a stereo microscope for observation.

The experimental results are shown in FIG. 13. On the 7th day, a block of calcific nodules stained red appeared in the HFMM/PEG2 hydrogel group; a patch of calcific nodules stained red appeared in the HFMM/PEG1 hydrogel group; gel was present in the GelMA group, while the PBS group had scattered calcified areas with cell outlines only. On the 14th day, the calcified areas of the rBMSCs in the HFMM/PEG1 and HFMM/PEG2 groups appeared in patches, while there were still scattered calcific nodules in the groups GelMA and PBS.

The experiments on the ALP staining and alizarin red dye further prove that the hyaluronic acid-based hydrogel of the present invention may accelerate the osteogenic differentiation of rBMSCs ex vivo and the formation of calcific nodules.

5.4 Test on the Cell Immunofluorescence of the rBMSCs after being Co-Cultured with the Hydrogel The rBMSCs in the culture flask were digested with a pancreatin, and inoculated onto a confocal dish by 500,000/well, and cultured in a 10% FBS-containing DMEM-F12 for 24 h; the HFMM/PEG1 hydrogel and the HFMM/PEG2 hydrogel synthesized in advance were placed into the wells and co-cultured, respectively; the equal volume of PBS and GelMA were added to the control group, respectively. After being cultured for 7 d and 14 d, respectively, the cells were immobilized with paraformaldehyde for 15 min, and permeated with 0.1% Triton-100 for 15 min. The BMP2 protein was stained green with Mouse-BMP2 primary antibody+Goat anti-mouse-AF488 secondary antibody; the OCN protein was stained red with Rabbit-OCN primary antibody+Goat anti-rabbit-AF647 secondary antibody; the cell nucleus was stained blue with DAPI. Each step of the staining should be washed for 3-4 times with PBS to remove the residual reagent of the previous step. A laser scanning confocal microscope was used for observation at last.

The experimental results show that after being co-cultured for 7 d, the expression of BMP2 and OCN by the cells is not significant in the PBS control group and GelMA group, indicating that there are a small number of cells for osteogenic differentiation in the PBS and GelMA co-culture systems. The expression of BMP2 and OCN in the HFMM/PEG1 hydrogel and HFMM/PEG2 hydrogel systems is much higher than that of the groups PBS and GelMA; the expression of BMP2 and OCN in the HFMM/PEG2 is up to the maximum. Meanwhile, the cellular morphology in the two groups of HFMM/PEG1 hydrogel and HFMM/PEG2 hydrogel is more inclined to a clostridial form, and more inclined to the cells for osteogenic differentiation. The DAPI cell nucleus labeling hints that the two groups of HFMM/PEG1 hydrogel and HFMM/PEG2 hydrogel have obvious cell growth aggregation for proliferation to form cell clusters.

14 d later after the co-culture, the expression of BMP2 in the groups PBS and GelMA increases; the BMP2-expressing cells are mainly polygonal and spheroidal and the cellular morphology is comparatively primitive. The expression of BMP2 and OCN in the HFMM/PEG1 hydrogel and HFMM/PEG2 hydrogel systems is still much higher than that of the groups PBS and GelMA.

5.5 Variation of the Transcriptional Level of the rBMSCs after being Co-Cultured with the Hydrogel The rBMSCs in the culture flask were digested with a pancreatin, and inoculated onto a 6-well plate by 500,000/well, and cultured in a 10% FBS-containing DMEM-F12 for 24 h; the HFMM/PEG1 hydrogel and the HFMM/PEG2 hydrogel synthesized in advance were placed into the wells and co-cultured, respectively; the equal volume of PBS and GelMA were added to the control group, respectively. Total RNA of the treated rBMSCs was extracted with an RNA extraction kit by a centrifugation column method at different time points. Total RNA was quantified by a Nanodrop RNA quantometer. The experiment was conducted for 3 times.

The above extracted Total RNA was divided into two copies; one was placed onto dry ice and sent for RNA-seq analysis. Another copy was subjected to reverse transcription into cDNA with a Takara reverse transcription kit, and then subjected to the subsequent RT-qPCR experiment.

The experimental results are shown in A of FIG. 14. On the 3rd day, the expression quantity of the Bmp2 gene in the two groups of HFMM/PEG1 hydrogel and HFMM/PEG2 hydrogel was significantly higher than that of the PBS control group and the GelMA group; there is statistical significance in difference; the expression quantity of the Bmp2 gene in the HFMM/PEG2 group is 1.85 times that in the control group. On the 7th day, the expression quantity of the Bmp2 gene in the two groups of HFMM/PEG1 hydrogel and HFMM/PEG2 hydrogel was still in the lead; and at this time, the expression quantity of BMP2 in the GelMA group increased to some extent and raised to small extent compared to the PBS group. On the 14 day, the expression quantity of the Bmp2 gene in the two groups of HFMM/PEG1 hydrogel and HFMM/PEG2 hydrogel increased markedly, being up to 2.96 and 3.46 times that in the PBS group, respectively, and also 2.01 and 3 times that in the GelMA group; moreover, there are statistical significances in difference between groups.

The experimental results are shown in B of FIG. 14. On the 3rd day, the expression quantity of the Ocn gene in the two groups of HFMM/PEG1 hydrogel and HFMM/PEG2 hydrogel was significantly higher than that of the PBS control group and the GelMA group, being about 2 times that in the PBS group. There is no statistical significance in the difference of the expression quantity of the Ocn between the two groups of HFMM/PEG1 hydrogel and HFMM/PEG2 hydrogel. On the 7th day, the expression quantity of the Ocn gene in the two groups of HFMM/PEG1 hydrogel and HFMM/PEG2 hydrogel was 10-15 times that in the PBS group. At this time, the expression quantity of the Ocn in the GelMA group slightly increased compared to the PBS group, which was consistent with the immunofluorescent result. On the 14 day, the expression quantity of the Ocn gene in the two groups of HFMM/PEG1 hydrogel and HFMM/PEG2 hydrogel was still much higher than that in the groups PBS and GelMA, being up to 12.5 and 20 times that in the PBS group, respectively, and moreover, there is a statistical significance in difference between groups. It's worth noting that the expression quantity of the Ocn gene in the GelMA group on the 14th day is lower than that on the 7th day, indicating that the hyaluronic acid-based hydrogel of the present invention plays an important role in promoting and maintaining the expression of the Ocn gene.

5.6 Variation of the Protein Level of the rBMSCs after being Co-Cultured with the Hydrogel The rBMSCs in the culture flask were digested with a pancreatin, and inoculated onto a 6-well plate by 500,000/well, and cultured in a 10% FBS-containing DMEM-F12 for 24 h; the HFMM/PEG1 hydrogel and the HFMM/PEG2 hydrogel synthesized in advance were placed into the wells and co-cultured, respectively; the equal volume of PBS and GelMA were added to the control group, respectively. RIPA was added to lyse the cells at different time points, a protease inhibitor and a phosphatase inhibitor were added at the same time to extract the total protein of the treated rBMSCs. The protein was quantified by a BCA protein quantification kit; Loading buffer was added to denature the protein for 10 min at 100° C. Loading was conducted for Western Blot (WB). The experiment was conducted for 3 times.

The experimental results show that compared with the PBS control group, after rBMSCs were co-cultured with the HFMM/PEG1 hydrogel and the HFMM/PEG2 hydrogel for 14 d, respectively, the levels of SMAD2/3, p-SMAD2/3, SMAD1/5/9, p-SMAD1/5/9, and TGFβ1 increased remarkably, which hints that the hyaluronic acid-based hydrogel of the present invention activates the TGF-β pathway to accelerate the osteoblast differentiation of rBMSCs.

In addition, this example further, by constructing a SD rat cranial defect model, proves that the hyaluronic acid-based hydrogel of the present invention may accelerate the cranial defect repair of the rat and the effect is more remarkable than that of the PBS control group.

GelMA served as the control group in this example, and the reasons are as follows: (1) the GelMA hydrogel has the similar structural features to the hyaluronic acid-based hydrogel of the present invention; (2) the GelMA hydrogel has the similar physical and chemical properties to the hyaluronic acid-based hydrogel of the present invention; and (3) the osteogenic effectiveness of the GelMA hydrogel has been widely validated. The present invention is mainly to study the bioinduction effect of the hyaluronic acid-based hydrogel on the rBMSCs, instead of the physical guidance of scaffold materials; therefore, the positive control of this experiment was GelMA; the physical guidance of the scaffold on bone defect repair may be eliminated.

Furthermore, the test data of this example indicates that the hyaluronic acid-based hydrogel of the present invention may significantly improve the activity, proliferation and ALP activity of rBMSCs; enhance the expression of osteogenic genes such as Ocn and Bmp2; increase the levels of OCN and BMP2 proteins, accelerate ex vivo mineralization; increase the levels of BMP2, SMAD2/3, and SMAD1/5/9 proteins as well as the levels of p-SMAD2/3 and p-SMAD1/5/9; activate the TGF-β pathway; facilitate the osteogenic differentiation of rBMSCs; and inhibit the osteoclastic differentiation of rBMSCs. By the test data and comparison with the GelMA control group, this example further indicates that the hyaluronic acid-based hydrogel of the present invention has a bioinduction effect on rBMSCs.

Example 6 Hemostatic Ability of the Hyaluronic Acid-Based Hydrogel

In this example, the hyaluronic acid-based hydrogel precursor solutions of Examples 1-2 was taken; deionized water in the component A was replaced into an equal volume of normal saline, and then the component A was mixed with the component B for testing; the hyaluronic acid-based hydrogel precursor solutions of Examples 1-2 were denoted as HFMM/PEG1 hydrogel and HFMM/PEG2 hydrogel, respectively. UV irradiation time of each group was 10 s, and the UV-light wavelength was 395 nm, and power was 50 $mW/cm^2$.

6.1 Hemolytic Property of the HFMM, 4-Arm Mercapto Polyethylene Glycol, and HFMM/PEG Hydrogel Precursor Solution Before the hydrogel was photo-cured, the precursor solution would keep contact with tissues; therefore, it needs to detect the hemolysis of each component in the hydrogel and the precursor solution. Sodium citrate anticoagulant rabbit whole blood was taken at a constant temperature of 37° C. and subpackaged into seven 2 mL EP tubes, by 0.2 mL per tube. Deionized water, normal saline, GelMA precursor solution, 2% HFMM solution, 500 mg/mL 4-arm mercapto polyethylene glycol solution, HFMM/PEG1 hydrogel precursor solution and the HFMM/PEG2 hydrogel precursor solution were added per EP tube by 0.8 mL, respectively. The materials were mixed with the blood well, and placed into a 37° C. incubator for incubation for 1 h, and centrifuged for 15 min at 3000 rpm; supernatant liquid was carefully absorbed and measured at a wavelength of 562 nm to obtain an absorbance, and then a hemolysis ratio was calculated. The operation was repeated for 3 times.

$$\text{Hemolysis ratio} = \frac{OD_{Sample} - OD_{normal\ saline}}{OD_{Deionized\ water} - OD_{normal\ saline}} \times 100\%$$

The experimental results show that normal saline serves as a negative control, and deionized water serves as a positive control; the results show the hemolysis ratios of the GelMA precursor solution, 2% HFMM solution, 500 mg/mL 4-arm mercapto polyethylene glycol solution, HFMM/PEG1 hydrogel precursor solution and the HFMM/PEG2 hydrogel precursor solution are all lower than 4%, remarkably lower than the positive control. The above indicates that the hyaluronic acid-based hydrogel precursor solution of the present invention has very high safety on red blood cells, and has a lower possibility to cause hemolysis. Hemolysis is shown in FIG. 15.

6.2 Hemolytic Property of the Hyaluronic Acid-Based Hydrogel

A 96-well plate was taken; deionized water, normal saline, GelMA precursor solution, HFMM/PEG1 hydrogel precursor solution, and the HFMM/PEG2 hydrogel precursor solution were added to the well of the 96-well plate by 200 μL, respectively; the material may be evenly paved at the bottom of the well plate and irradiated by UV light for 10 s. Sodium citrate anticoagulant rabbit whole blood was taken at a constant temperature of 37° C. and 200 μL were added per well, and placed into a 37° C. incubator for incubation for 1 h, and centrifuged for 15 min at 3000 rpm; erythrocyte sedimentation and hemolysis on the gel were scanned and recorded; the supernatant liquid was absorbed carefully, and measured at wavelength of 562 nm to obtain an absorbance. The operation was repeated for 3 times. The calculation formula of the hemolysis ratio is the same as above.

The experimental results show that when the hydrogel is gelatinized and coagulated, the hemolysis ratios of the GelMA hydrogel, HFMM/PEG1 hydrogel, and the HFMM/PEG2 hydrogel are all lower than 5%, and the hemolysis ratio of the hydrogel is lower than that of the precursor solution thereof.

6.3 Ex Vivo Coagulation 4 mL sodium citrate anticoagulant rabbit whole blood was taken at a constant temperature of 37° C. into a 15 mL centrifugal tube; 400 μL of 0.2 M $CaCl_2$) solution (prepared by normal saline) was added for activation; the cells were pipetted and mixed well, and the rapidly subpackaged into six 1.5 mL EP tubes, by 0.5 mL per tube. Normal saline, GelMA precursor solution, 2% HFMM solution, 4-arm mercapto polyethylene glycol solution, HFMM/PEG1 hydrogel precursor solution and the HFMM/PEG2 hydrogel precursor solution were added per EP tube by 100 μL, respectively. The tubes were placed into a mute mixer such that the materials were mixed with the blood well; time when the blood stopped flowing in the tube was recorded, i.e., the ex vivo coagulation time of the gel precursor solution and the process components. The operation was repeated for 3 times.

The experimental results are shown in A of FIG. 16. Compared with the normal saline group, the GelMA precursor solution group has no statistical significance in the difference of the ex vivo coagulation time; the coagulation time of the 2% HFMM solution, the HFMM/PEG1 hydrogel precursor solution, and the HFMM/PEG2 hydrogel precursor solution is 50% above shorter than that of the GelMA group and the normal saline control group, of which the HFMM/PEG2 hydrogel precursor solution achieves the optimal coagulation-promoting effect; the blood coagulation time is 201 s, shortened by 72%.

A 96-well plate was taken; GelMA precursor solution, HFMM/PEG1 hydrogel precursor solution, and the HFMM/PEG2 hydrogel precursor solution were added to the well of the 96-well plate by 100 μL, respectively; the material may be evenly paved at the bottom of the well plate and irradiated by UV light for 10 s, and then taken out carefully. 2 mL sodium citrate anticoagulant rabbit whole blood was taken at a constant temperature of 37° C. into four 4 mL centrifugal tubes; 60 μL of 0.1 M $CaCl_2$ solution (prepared by normal saline) was added for activation; the cells were pipetted and mixed well, and the prepared hydrogel above was rapidly added; 50 μL normal saline was added to the control group. The tubes were placed into a mute mixer; time when the blood stopped flowing in the tube was recorded, i.e., the ex vivo coagulation time of the hydrogel. The operation was repeated for 3 times.

The experimental results are shown in B of FIG. 16. The GelMA hydrogel similarly has no coagulation-accelerating function after gelation; the ex vivo blood coagulation time in the HFMM/PEG1 hydrogel and the HFMM/PEG2 hydrogel may be shortened similarly after gelation, of which the blood coagulation time in the HFMM/PEG2 hydrogel is shortened by 21%, and the coagulation effect is better.

6.4 Hemostasis Experiment of a Rat Femoral Venipuncture Model

Rats were anesthetized with Zoletil; inner thigh and inguinal region were cut off. Note to not perforate abdominal cavity. Rat femoral vein was isolated carefully. Femoral vein was punctured with a No. 25 syringe needle; if there was blood after pumping back, smooth puncture was proved; the HFMM/PEG2 hydrogel was sprayed immediately; normal saline and GelMA (where the GelMA mobility was low and thus added dropwise with a pipette) were used in the control group. Immediate hemostasis effect was observed after UV light polymerization. The rat wound was then sutured layer by layer; the survival condition of the rats was recorded after operation.

The experimental results are shown in FIG. 17. Y-coordinate of the a of FIG. 17 represents bleeding volume; Y-coordinate of the b of FIG. 17 represents blood coagulation time; Y-coordinate of the c of FIG. 17 represents a survivor curve; the hemostatic effect is up to the optimal after puncture and using the HFMM/PEG2 hydrogel; 12 h later after the operation, the rat has the highest survival rate, which is significantly higher than that in the GelMA group and the normal saline group. The hemostatic effect in the GelMA group is transitory after puncture and slightly stronger than that in the normal saline group; but when it is very easy to induce bleeding again when in contact with the surroundings of the puncture point.

6.5 Hemostasis Experiment for a Fatal Liver Injury Model

Rats were anesthetized with Zoletil; the abdomen of each rat was cut off from the middle part below the xiphoid. Note to not perforate chest. Liver was clamped with towel forceps and exposed by means of the retraction of the incision edge, and cushioned with a sterile filter paper below the liver. The edge of the liver was cut off with surgical scissors; the clipping path had a length of about 2 cm, and then the HFMM/PEG2 hydrogel was sprayed immediately; normal saline was used in the control group. Immediate hemostasis effect was observed after UV irradiation. Two minutes later, the bleeding volume of the rats was measured. The liver tissue together with the material were then plugged back to the abdominal cavity; the abdomen wound was sutured layer by layer; the survival condition of the rats was recorded after operation.

The experimental results are shown in FIG. 18. Y-coordinate of the a of FIG. 18 represents bleeding volume; Y-coordinate of the b of FIG. 18 represents blood coagulation time; Y-coordinate of the c of FIG. 18 represents a survivor curve. After the fatal liver injury model was built, bleeding was stopped rapidly by spraying the HFMM/PEG2 hydrogel, and the hemostatic effect is stronger than that in the normal saline group. The rat's survival rate is up to the highest 12 weeks later after the operation.

6.6 Investigation of the Hemostatic Mechanism 6.6.1 Erythrocyte Adsorption Rate

A 96-well plate was taken; GelMA precursor solution, HFMM/PEG1 hydrogel precursor solution, and the HFMM/PEG2 hydrogel precursor solution were added to the well of the 96-well plate by 50 μL, respectively; the material may be evenly paved at the bottom of the well plate and irradiated by UV light for 10 s. Sodium citrate anticoagulant rabbit whole blood was taken at a constant temperature of 37° C. and centrifuged for 15 min at 3000 rpm to prepare a 5% red cell suspension (dissolved by normal saline). 10 μL of 5% red cell suspension was added to the middle position of the gel per well, standing for 60 min. 100 μL normal saline was slightly added, and placed onto a table concentrator, and shaken slowly for 5 min; 20 μL supernatant liquid was absorbed and transferred into a new 96-well plate; 100 μL deionized water was added to the new plate which was then slowly shaken on the table concentrator for 10 min. The absorbance was then measured at a wavelength of 562 nm. The erythrocyte adsorption rate of the hydrogel was calculated. The operation was repeated for 3 times.

$$\text{Erythrocyte adsorption rate} = \left(1 - \frac{OD_{Sample}}{OD_{Blank\ plate}}\right) \times 100\%$$

The experimental results show that the erythrocyte adsorption rate in the HFMM/PEG1 hydrogel group is (27.54±2.72%); the erythrocyte adsorption rate in the HFMM/PEG2 hydrogel group is (36.58±4.61%), which are significantly higher than that in the GelMA group (9.87±1.57). It indicates that the hyaluronic acid-based hydrogel of the present invention may accelerate erythrocyte adsorption.

6.6.2 Analysis on Erythrocyte Aggregation

A 96-well plate was taken; GelMA precursor solution, HFMM/PEG1 hydrogel precursor solution, and the HFMM/PEG2 hydrogel precursor solution were added to the well of the 96-well plate by 50 μL, respectively, and irradiated by UV light for 10 s, to form the GelMA gel, HFMM/PEG1 gel, and HFMM/PEG2 gel; 50 μL normal saline was added per well. Normal saline, GelMA precursor solution, 2% HFMM solution, 500 mg/mL 4-arm mercapto polyethylene glycol solution, HFMM/PEG1 hydrogel precursor solution and the HFMM/PEG2 hydrogel precursor solution were added to other wells of the 96-well plate by 50 μL, respectively. Sodium citrate anticoagulant rabbit whole blood was taken at a constant temperature of 37° C. and centrifuged for 15 min at 3000 rpm to prepare a 5% red cell suspension (dissolved by normal saline); the suspension was rapidly added to the 96-well plate, 5 μL per well. The well plate was oscillated for 15 s by a plate oscillator and mixed well; the aggregation behavior of red blood cells was immediately observed with an inverted microscope.

The experimental result before UV irradiation is shown in FIG. 19. In FIG. 19, a of FIG. 19 represents normal saline; b of FIG. 19 represents the GelMA precursor solution; c of FIG. 19 represents the 2% HFMM precursor solution; d of FIG. 19 represents the represents the PEG; e of FIG. 19 represents the HFMM/PEG1 precursor solution; f of FIG. 19 represents the HFMM/PEG2 precursor solution; all the scales represent 400 m. As can seen from FIG. 19, compared with the normal saline group, the diluted red blood cells in the 2% HFMM precursor solution and the GelMA precursor solution show aggregation, indicating that both HFMM and GelMA have certain erythrocyte aggregation effects. In the HFMM/PEG1 hydrogel precursor solution and the HFMM/PEG2 hydrogel precursor solution, the erythrocyte aggregation is more obvious.

After gelation under UV irradiation, the experimental results are shown in FIG. 20. In FIG. 20, a of FIG. 20 represents normal saline; b of FIG. 20 represents the GelMA hydrogel; c of FIG. 20 represents the HFMM/PEG1 hydrogel; d of FIG. 20 represents the HFMM/PEG2 hydrogel; all the scales represent 400 m. As can seen from FIG. 20, the erythrocyte aggregation effect on the surface of the GelMA hydrogel is weak; while the HFMM/PEG1 hydrogel and the HFMM/PEG2 hydrogel still keep good erythrocyte aggregation effect on the surface thereon.

A 96-well plate was taken; GelMA precursor solution, HFMM/PEG1 hydrogel precursor solution, and the HFMM/PEG2 hydrogel precursor solution were added to the well of the 96-well plate, respectively; the material may be evenly paved at the bottom of the well plate and irradiated by UV light for 10 s; the prepared hydrogel slices were taken out carefully. Sodium citrate anticoagulant rabbit whole blood was taken at a constant temperature of 37° C. and centrifuged for 15 min at 3000 rpm to prepare a 5% red cell suspension (dissolved by normal saline); the suspension was rapidly added to the hydrogel slice, 50 μL per well. After standing for 60 min, the above sample was soaked with paraformaldehyde for 2 h, dewatered by ethanol in gradients, dried, placed onto a sample table, and subjected to metal spraying, and observed under a scanning electron microscope.

The experimental results are shown in FIG. 21. By SEM image, it was observed that the erythrocyte aggregation on the surface of the HFMM/PEG hydrogel is stronger than that on the GelMA hydrogel, where the erythrocyte aggregation on the HFMM/PEG2 hydrogel is stronger than that on the HFMM/PEG1 hydrogel. The above two groups are stronger than the GelMA hydrogel group.

6.6.3 Platelet Adsorption Rate and Aggregation Analysis

Sodium citrate anticoagulant rabbit blood was taken and centrifuged for 5 min at 1500 rpm; supernatant liquid was collected to obtain platelet rich plasma (PRP). A 96-well plate was taken; GelMA precursor solution, HFMM/PEG1 hydrogel precursor solution, and the HFMM/PEG2 hydrogel precursor solution were added to the well of the 96-well plate by 50 μL, respectively, and irradiated by UV light for 10 s, to form the GelMA gel, HFMM/PEG1 gel, and HFMM/PEG2 gel; 20 μL PRP was added per well, standing for 60 min at 37° C. The gel surface was cleaned carefully with normal saline to remove the unadhered blood platelet. After removing normal saline, 50 μL of 1% Trition X-100 normal saline was added per well for pyrolysis for 60 min. 10 μL of lysis solution was taken and transferred into a new 96-well plate; 100 μL LDH working solution was added per well, an absorbance was then measured at a wavelength of 450 nm, and the platelet adsorption rate of the hydrogel was calculated. PRP was selected as a control. The operation was repeated for 3 times.

$$\text{Platelet adsorption rate} = \left(1 - \frac{OD_{Sample}}{OD_{Control}}\right) \times 100\%$$

The experimental results show that the platelet adsorption capacities of the HFMM/PEG1 hydrogel and the HFMM/PEG2 hydrogel are obviously stronger than that of the GelMA hydrogel. There is no statistical significance in the difference of the platelet adsorption capacity between the two hyaluronic acid-based hydrogels of the HFMM/PEG1 hydrogel and the HFMM/PEG2 hydrogel.

A 96-well plate was taken; GelMA precursor solution, HFMM/PEG1 hydrogel precursor solution, and the HFMM/PEG2 hydrogel precursor solution were added to the well of the 96-well plate, respectively; the material may be evenly paved at the bottom of the well plate and irradiated by UV light for 10 s; the prepared hydrogel slices were taken out carefully. Sodium citrate anticoagulant rabbit whole blood was taken at a constant temperature of 37° C. and centrifuged for 5 min at 1500 rpm to prepare platelet rich serum (PRP); the PRP was rapidly added to the hydrogel slice, 50 μL per well. After standing for 60 min, the above sample was soaked with paraformaldehyde for 2 h, dewatered by ethanol in gradients, dried, placed onto a sample table, and subjected to metal spraying, and observed under a scanning electron microscope.

The experimental results are shown in FIG. 22. By SEM image, it was observed that the erythrocyte aggregation on the surface of the HFMM/PEG hydrogels is stronger than that on the GelMA hydrogel.

6.6.4 Activation of the Coagulation Pathway

Prothrombin time (PT) and activated partial thromboplastin time (APTT) are important indicators to judge endogenous and exogenous coagulation pathways. PT is used for exogenous coagulation, and APTT is used for endogenous coagulation.

Fresh sodium citrate anticoagulant rabbit blood was taken and centrifuged for 15 min at 3000 rpm; supernatant liquid was collected to obtain platelet-poor plasma (PPP). 80 μL of PPP preheated in a 37° C. water bath and 20 μL of each group of sample (including: normal saline, GelMA precursor solution, 2% HFMM, 4-arm mercapto polyethylene glycol, HFMM/PEG1 hydrogel precursor solution, HFMM/PEG2 hydrogel precursor solution, GelMA hydrogel block, HFMM/PEG1 hydrogel block, or HFMM/PEG2 hydrogel block, respectively) were added to 100 L ellagic acid solution, kept in a 37° C. water bath for 5 min, intermittently mixed well for several times, and then 100 μL of $CaCl_2$ (25 mM) solution preheated at 37° C. was added, and APTT timekeeping was started immediately. The solution was placed into a water bath kettle during the process and the occurrence time of the fibrin filament (coagulated at the initial stage of appearing the turbid state) was observed, and the operation was repeated for 3 times.

The experimental results are shown in A of FIG. 23. APTT may not be shortened in the groups GelMA precursor solution, GelMA hydrogel block, and 4-arm mercapto polyethylene glycol; compared with the normal saline group, the APTT of the 4-arm mercapto polyethylene glycol is extended 8.9%, indicating that the 4-arm mercapto polyethylene glycol slightly inhibits the endogenous coagulation pathway. The APTT is shortened most obviously in the 2% HFMM group, 60.5% plasma coagulation time is shortened effectively compared to the normal saline group. APTT in the groups of HFMM/PEG2 hydrogel precursor solution, HFMM/PEG1 hydrogel precursor solution, HFMM/PEG2 hydrogel block, and the HFMM/PEG1 hydrogel block is also shortened to some extent, by 49.2%, 46.0%, 25.8%, and 18.5%, respectively. It indicates that these components may significantly activate the endogenous coagulation pathway.

Fresh sodium citrate anticoagulant rabbit blood was taken and centrifuged for 15 min at 3000 rpm; supernatant liquid was collected to obtain platelet-poor plasma (PPP). 80 μL of PPP preheated in a 37° C. water bath and 20 μL of each group of sample (including: normal saline, GelMA precursor solution, 2% HFMM, 4-arm mercapto polyethylene glycol, HFMM/PEG1 hydrogel precursor solution, HFMM/PEG2 hydrogel precursor solution, GelMA hydrogel block, HFMM/PEG1 hydrogel block, or HFMM/PEG2 hydrogel block, respectively) were added to 100 μL PT reagent, kept in a 37° C. water bath for 5 min, intermittently mixed well for several times, and then 100 μL of $CaCl_2$ (25 mM) solution preheated at 37° C. was added, and PT timekeeping was started immediately. The solution was placed into a water bath kettle and continuously oscillated during the process; the PPP coagulation time was calculated; the operation was repeated for 3 times.

The experimental results are shown in B of FIG. 23. Compared with NS, the 4-arm mercapto polyethylene glycol may shorten PT for about 3 s, which indicates that the 4-arm mercapto polyethylene glycol may activate the exogenous coagulation pathway. There is no statistical significance in the difference of the PT in each group of the HFMM/PEG2 hydrogel precursor solution, HFMM/PEG1 hydrogel precursor solution, 2% HFMM, GelMA precursor solution, GelMA hydrogel block, HFMM/PEG1 hydrogel block, and HFMM/PEG2 hydrogel block, which indicates that these components have no effect on the exogenous pathway.

The hyaluronic acid-based hydrogel of the present invention is grafted with a methacrylate group and a norbornyl-like group; the hexose ring on the backbone of the hyaluronic acid is still rich in hydroxyl, which is beneficial for vasoconstriction; the hyaluronic acid-based hydrogel has good adsorption capacity to blood platelets and red blood cells, thus forming the initial blood clot, which is associated with the structures of the methacrylate group and the norbornene-like group. It is speculated that negatively charged blood platelets and red blood cells are adsorbed by the positive charges carried by the methacrylate group and the norbornyl-like group.

The experimental results of this example show that the hyaluronic acid-based hydrogel of the present invention and its precursor solution activate exogenous and endogenous pathways in coagulation cascade reactions by accelerating blood platelet adsorption and erythrocyte aggregation, and form a physical barrier via the transformation of an aqueous phase into a gel phase, thus achieving in vivo and ex vivo rapid hemostasis.

Example 7 Skin Defect Repair Capacity of the Hyaluronic Acid-Based Hydrogel

In this example, the hyaluronic acid-based hydrogel precursor solution of Examples 1-2 was taken; deionized water in the component A was replaced into an equal volume of normal saline, and then the component A was mixed with the component B for testing; the hyaluronic acid-based hydrogel precursor solution of Examples 1-2 was denoted as HFMM/PEG1 hydrogel and HFMM/PEG2 hydrogel, respectively.

UV irradiation time of each group was 10 s, and the UV-light wavelength was 395 nm, and power was 50 mW/cm$^2$.

7.1 Test on the Cell Proliferation of the Raw264.7, HUVEC, and L929 after being Co-Cultured with the Hydrogel The proliferation ability of the Raw264.7, HUVEC, and L929 was detected by a CCK-8 kit. The Raw264.7 cells in the culture flask were scraped with a cell scraper; the HUVEC and L929 cells were digested with a pancreatin, and inoculated onto a 48-well plate by 100,000/well, Raw264.7 and L929 were cultured in a 10% FBS-containing DMEM, and the HUVEC was cultured in an ECM endothelial medium; after 24-hour culture, the HFMM/PEG hydrogel synthesized in advance was placed into the wells and co-cultured; the equal volume of PBS and GelMA hydrogel were added to the control group, respectively. 1 d later, 30 μL CCK-8 test solution was added per well and continuously incubated for 2 h, then 100 μL supernatant was taken out per well and transferred into a 96-well plate; an absorbance was detected at 450 nm.

The experimental results show that the GelMA hydrogel has no proliferative activity to Raw264.7, HUVEC, and L929 in a short time; the HFMM/PEG1 hydrogel and the HFMM/PEG2 hydrogel may significantly enhance the proliferative activity of Raw264.7, HUVEC, and L929, which indicates that the hyaluronic acid-based hydrogel of the present invention has acceleration on the proliferation ability of the cells (Raw264.7, HUVEC, and L929).

7.2 Test on the Immunofluorescence of the Raw264.7, HUVEC, and L929 after being Co-Cultured with the Hydrogel Raw264.7 cells in the culture flask were scraped with a cell scraper, inoculated on a confocal dish by 50,000/well; and the Raw264.7 were cultured with a 10% FBS-containing DMEM for 24 h and divided into 8 groups in total. The PBS group, GelMA group, HFMM/PEG1 hydrogel group, and HFMM/PEG2 hydrogel group were used to study the effects of the HFMM/PEG hydrogel on macrophage differentiation. The lipopolysaccharide (LPS) group (treated by 1 μg/mL LPS) was used to study the status of macrophage when simulating bacterial infection with LPS; the LPS+HFMM/PEG2 group (1 μg/mL LPS and HFMM/PEG2 hydrogel were added to the cell culture system at the same time) was used to study the status of macrophage when LPS and HFMM/PEG2 are combined for action, so as to ex vivo simulate bacterial infection when HFMM/PEG2 was used simultaneously. The FLPS+HFMM/PEG2 group (pretreated by 1 g/mL LPS for 3 h; washed with PBS for 5 times, and then the HFMM/PEG2 hydrogel was added; FLPS refers that LPS was first used for pretreatment, and then interacted with the hydrogel) was used to study the status of macrophage when the HFMM/PEG2 was used after LPS treatment, so as to ex vivo simulate that HFMM/PEG2 was applied after bacterial infection. The IL-4 group (50 ng/mL) served as an M2-polarized positive control group. After being continuously cultured for 1 d, the cells were immobilized with paraformaldehyde for 15 min, and permeated with 0.1% Triton-100 for 15 min. The CD206 protein was stained green with Mouse-CD206-FITC directly-labeled primary antibody; the iNOS protein was stained red with Rabbit-OCN primary antibody+Goat anti-rabbit-AF647 secondary antibody; the cell nucleus was stained blue with DAPI. Each step of the staining should be washed for 3-4 times with PBS to remove the residual reagent of the previous step. A laser scanning confocal microscope was used for observation at last.

The experimental results show that the iNOS level does not increase remarkably during the co-culture process of the Raw264.7 with the GelMA hydrogel, HFMM/PEG1 hydrogel, and the HFMM/PEG2 hydrogel, indicating that the GelMA hydrogel, HFMM/PEG1 hydrogel, and the HFMM/PEG2 hydrogel will not directly induce the M1 polarization of Raw264.7, not actively causing inflammatory response. Compared with the PBS control group and the GelMA hydrogel, the hyaluronic acid-based hydrogel of the present invention may remarkably increase the expression of Raw264.7 CD206.

In addition, the 1 μg/mL of LPS treatment successfully induced the M1 polarization of Raw264.7 and simulated the real status of the skin defect. In the presence of the HFMM/PEG2 hydrogel, the iNOS expression quantity down-regulated obviously both in the group treated with LPS simultaneously and the group treated with LPS first, which proves that the HFMM/PEG2 hydrogel has a good inhibition effect on the M1 polarization of the Raw264.7. Even though the HFMM/PEG2 hydrogel worked later than LPS (the FLPS+HFMM/PEG2 group), it may still inhibit the M1 polarization of the Raw264.7. The CD206 results indicate that in the existence of LPS, the HFMM/PEG2 hydrogel still shows remarkable acceleration on the M2 polarization of the Raw264.7.

The HUVEC in the culture flask were digested with a pancreatin, and inoculated onto a confocal dish by 100,000/well; the HUVEC were cultured in an ECM endothelial medium for 24 h; the HFMM/PEG hydrogel synthesized in advance was placed into the confocal dish and co-cultured; the equal volume of PBS and GelMA hydrogel were added to the control group, respectively. After being continuously cultured for 1 d, the cells were immobilized with paraformaldehyde for 15 min, and permeated with 0.1% Triton-100 for 15 min. The PECAM protein was stained green by Mouse-PECAM-1 primary antibody+Goat anti-mouse-AF488 secondary antibody; cell nucleus was stained blue with DAPI. Each step of the staining should be washed for 3-4 times with PBS to remove the residual reagent of the previous step. A laser scanning confocal microscope was used for observation at last.

The experimental results show that compared with the PBS group and the GelMA group, the HUVEC in the HFMM/PEG hydrogel co-culture system may express more PECAM-1 proteins, where the acceleration of the HFMM/PEG2 hydrogel on the expression of the angiogenic associated proteins is stronger than that of the HFMM/PEG1 hydrogel.

L929 cells in the culture flask were digested with a with pancreatin, and inoculated onto a confocal dish by 50,000/well; and the L929 cells were cultured with a 10% FBS-containing DMEM for 24 h and divided into 7 groups in total. The PBS group, GelMA group, HFMM/PEG1 hydrogel group, and HFMM/PEG2 hydrogel group were used to explore the effects of the HFMM/PEG hydrogel on L929 cell function, and to study the effects of the PEG content of the HFMM/PEG hydrogel on L929. The TNFα group (treated by 2.5 ng/mL TNFα only) was used to simulate the ex vivo situation under the inflammatory state without the use of the hydrogel. The TNFα+HFMM/PEG2 group (2.5 ng/mL TNFα and HFMM/PEG2 hydrogel were added to a cell culture system at the same time) was used to study the status of macrophage when TNFα was combined with HFMM/PEG2 for action, so as to ex vivo simulate bacterial infection when HFMM/PEG2 was used simultaneously. The FTNFα+HFMM/PEG2 group (pretreated by 2.5 ng/mL TNFα for 3 h, and pretreated for 3 h, washed with PBS for 5 times, and then the HFMM/PEG2 hydrogel was added) was used to study the status of macrophage when the HFMM/PEG2 was used after the TNFα treatment, so as to ex vivo simulate that HFMM/PEG2 was applied after bacterial infection. After being continuously cultured for 1 d, the cells were immobilized with paraformaldehyde for 15 min, and permeated with 0.1% Triton-100 for 15 min. Type I collagen was stained green with Mouse-COL1A1 primary antibody+Goat anti-mouse-AF488 secondary antibody; the iNOS protein was stained red with Rabbit-iNOS primary antibody+Goat anti-rabbit-AF647 secondary antibody; the cell nucleus was stained blue with DAPI. Each step of the staining should be washed for 3-4 times with PBS to remove the residual reagent of the previous step. A laser scanning confocal microscope was used for observation at last.

The experimental results show that compared with the PBS control group, the protein level of COL1A1 in the GelMA hydrogel group does not increase remarkably; after the L929 cells were co-cultured with the GelMA hydrogel, HFMM/PEG1 hydrogel, and the HFMM/PEG2 hydrogel, the cellular iNOS protein level has no significant difference, which indicates that the GelMA hydrogel, HFMM/PEG1 hydrogel, and the HFMM/PEG2 hydrogel will not actively activate the TNFα pathway of L929 cells to cause inflammatory response. After the L929 cells were co-cultured with the HFMM/PEG1 hydrogel and the HFMM/PEG2 hydrogel, the protein level of COL1A1 increases remarkably, indicating that the hyaluronic acid-based hydrogel of the present invention may significantly accelerate the L929 to secrete the type I collagenous fiber.

In addition, 2.5 ng/mL of the TNFα treatment smoothly causes the inflammatory response of L929, and the iNOS protein level increases remarkably. In the group simultaneously treated with TNFα and HFMM/PEG2 hydrogel, the iNOS protein level down-regulated remarkably, indicating that the hyaluronic acid-based hydrogel of the present invention may have a good inhibition effect on the L929 inflammatory response induced by TNFα. Even though the HFMM/PEG2 hydrogel worked later than TNFα, it may still inhibit the L929 inflammatory response induced by TNFα.

7.3 Flow Cytometry Analysis on the Raw264.7 after being Co-Cultured with the Hydrogel Raw264.7 cells in the culture flask were scraped with a cell scraper, and inoculated onto a 6-well plate by 500,000/well; and the cells were cultured with a 10% FBS-containing DMEM for 24 h and divided into 6 groups, namely, the PBS group, HFMM/PEG2 hydrogel group, LPS group (treated with 1 μg/mL LPS), LPS+HFMM/PEG2 group (1 μg/mL LPS and HFMM/PEG2 hydrogel were added to a cell culture system at the same time), FLPS+HFMM/PEG2 group (pretreated with 1 μg/mL LPS for 3 h, washed with PBS for 5 times, and the HFMM/PEG2 hydrogel was added), and the IL-4 group (treated with 50 ng/mL IL-4), and contiguously cultured for 1 d. All the subsequent operations were conducted on ice in the dark. Each group of cells were scraped with a cell scraper, and washed twice with cold PBS, and centrifuged, then immobilized for 15 min with 100 μL paraformaldehyde. After the cells were washed again, Intracellular Straining and Premature Buffer was used for rupture of membranes for 20 min, and then the cells were subjected to rupture of membranes for 20 min after removing the supernatant by centrifugation. The cells were then blocked with a FcR sealing agent for 10 min. Rabbit anti-iNOS antibody and Mouse anti-CD206-FITC antibody were then diluted with an antibody diluent, and cells were stained for 30 min. After the cells were washed with Intracellular Straining and Premature Buffer for 3 times, and then iNOS was stained with Goat anti-Rabbit antibody-AF647 secondary antibody for 30 min, then the cells were washed with Intracellular Straining and Premature Buffer for 3 times, and resuspended, and loaded on a machine for detection. iNOS simple-staining group, CD206 simple-staining group and blank control group were set for the experiment at the same time.

The experimental results indicate that after co-culture with the HFMM/PEG2 hydrogel, the number of $iNOS^-/CD206^+$ cells increases remarkably and accounts for about 1.8% of the total cell count; even though it is 3.5% lower than that in the positive control group (IL-4 group), it is still 1.62 times that in the PBS group.

LPS successfully induced the M1 polarization of Raw264.7; the number of $iNOS^+/CD206^-$ cells is up to the maximum in the LPS group, being about 83%. When the LPS and HFMM/PEG2 hydrogel acted on the Raw264.7 at the same time, the HFMM/PEG2 hydrogel showed inhibition on the LPS-induced M1 polarization; the number of $iNOS^+/CD206^-$ cells decreases remarkably, reducing to 81% from 83%. The decreased $iNOS^+/CD206^-$ cells were not completely transformed into $iNOS^-/CD206^+$ cells, and most of them existed in the form of $iNOS^-/CD206^-$ cells. It also indirectly indicates that the HFMM/PEG2 hydrogel may inhibit the Raw264.7 from differentiating into M1 macrophages more in the environment of LPS.

Furthermore, in the FLPS+HFMM/PEG2 group induced with LPS first and co-cultured with the HFMM/PEG2 hydrogel, the number of $iNOS^+/CD206^-$ cells decreases to 66%, and its decreasing amplitude approaches 20% compared to the LPS group. The number of $iNOS^-/CD206^+$ cells also increases remarkably, which hints that the HFMM/PEG2 hydrogel still has very strong acceleration of M2 polarization to the LPS-induced Raw264.7.

7.4 Test on the Angiogenic Capacity of the HUVEC after being Co-Cultured with the Hydrogel A Corning matrigel (Cat. 354234) was used and had a concentration of 10 mg/mL. The matrigel was defrosted in a 4° C. refrigerator; a PerkinElmer flat-bottom 96-well plate was put on ice, and 80 μL matrigel liquid was added per well. Note that all the pipette heads need to be precooled. Sterile operation should be noted. The plate was slightly vibrated such that the matrigel was evenly paved at the bottom of the well. The plate was then placed into an incubator for 30 min until the matrigel was gelled completely. The HUVEC in the culture flask were digested with a pancreatin, and diluted by an ECM endothelial medium, and the final inoculum density was 30,000/well. The plate was immediately put to a high content meter and kept for 30 min, after all the cells were sedimented, PBS, GelMA hydrogel, HFMM/PEG1 hydrogel, and HFMM/PEG2 hydrogel were added, respectively for culture for 24 h; the shooting interval was 0.5 h.

The experimental results are shown in FIG. 24. Compared with the PBS control group, the GelMA hydrogel has a transient angiogenesis effect within 4 h. The blood vessel formed suffered rapid apoptosis over time. The HFMM/PEG1 hydrogel and the HFMM/PEG2 hydrogel have strong ex vivo angiogenic capacity of HUVEC, and maintain the physiological activity of HUVEC continuously, and significantly inhibit the apoptosis of HUVEC. 24 h later, the blood vessels formed by the HFMM/PEG1 hydrogel and the HFMM/PEG2 hydrogel were kept intact.

7.5 Variation of the Transcriptional Levels of the Raw264.7, HUVEC, and L929 after being Co-Cultured with the Hydrogel Total RNA of the treated Raw264.7, HUVEC, and L929 was extracted with an RNA extraction kit by a centrifugation column method. Total RNA was quantified by a Nanodrop One ultraviolet-visible light spectrometer. The experiment was conducted for 3 times. Takara reverse transcription kit was used for reverse transcription, and then the obtained cDNA was used for the subsequent RT-qPCR test.

The experimental results indicate that the HFMM/PEG1 hydrogel and the HFMM/PEG2 hydrogel may remarkably down-regulate the mRNA expression levels of the iNOS and Tnfα of the Raw264.7; the mRNA expression quantity of iNOS is a quarter of the PBS group and the GelMA group. The HFMM/PEG1 hydrogel and the HFMM/PEG2 hydrogel may further remarkably up-regulate the mRNA expression quantity of Raw264.7 Cd206.

Additionally, under the condition of ex vivo simulating real skin defect, 1 μg/mL LPS may remarkably up-regulate the expression of the Raw264.7 iNOS, and remarkably down-regulate the expression of the Cd206. In the above context, the HFMM/PEG hydrogel may inhibit the M1 polarization of the LPS-induced Raw264.7, inhibit the expression of the iNOS, remarkably accelerate the expression of the Cd206, and accelerate its M2 polarization. Even though the cells were induced with 1 μg/mL LPS in advance, the HFMM/PEG hydrogel may still remarkably inhibit the M1 polarization of the Raw264.7 and accelerate its M2 polarization.

The HFMM/PEG1 hydrogel and the HFMM/PEG2 hydrogel may remarkably up-regulate expression quantity of the genes ICAM-1, VCAM-1, VEGFA, and IL-8, and accelerate vascularization of HUVEC. The expression quantity of the genes ICAM-1, VCAM-1, VEGFA, and IL-8 in the HFMM/PEG1 hydrogel group was 4.57, 1.52, 3.61, and 3.93 times that in the PBS control group, respectively. The expression quantity of the genes ICAM-1, VCAM-1, VEGFA, and IL-8 in the HFMM/PEG2 hydrogel group was 11.87, 2.34, 7.59, and 8.96 times that in the PBS control group, respectively. There is no statistical significance in the difference of expression quantity between each group of the eNOS gene. There is no significant difference in the expression quantity of the vascularization-associated genes in the groups GelMA and PBS.

Compared with the groups PBS and GelMA, both the HFMM/PEG1 hydrogel and the HFMM/PEG2 hydrogel may remarkably down-regulate the expression quantity of iNOS in L929 cells, and remarkably up-regulate the expression quantity of Col1a1; there are statistical significances in the difference between groups.

2.5 ng/mL TNFα may remarkably up-regulate the expression of the L929 iNOS and remarkably down-regulate the expression of its Col1a1. In the group treated with TNFα and HFMM/PEG2 hydrogel simultaneously, the HFMM/PEG2 hydrogel may remarkably inhibit the high expression of iNOS in the TNFα-induced L929, and remarkably accelerate the expression of Col1a1, and promote the secretion of extracellular matrix. Even though the cells were induced with TNFα in advance, the HFMM/PEG2 hydrogel may still remarkably inhibit the expression of L929 iNOS and accelerate the expression of Col1a1. The above is consistent with the immunofluorescence result of the L929 cell.

7.6 Analysis on the Transcriptomes of the Raw264.7, and HUVEC after being Co-Cultured with the Hydrogel Raw264.7 cells in the culture flask were scraped with a cell scraper, and inoculated onto a 6-well plate by 500,000/well; and the cells were cultured with a 10% FBS-containing DMEM for 24 h and divided into 5 groups, namely, the PBS group, HFMM/PEG2 hydrogel group, LPS group (treated with 1 μg/mL LPS), LPS+HFMM/PEG2 group (1 μg/mL LPS and HFMM/PEG2 hydrogel were added to a cell culture system at the same time), FLPS+HFMM/PEG2 group (pretreated with 1 μg/mL LPS for 3 h, washed with PBS for 5 times, and the HFMM/PEG2 hydrogel was added), and contiguously cultured for 1 d, and then subjected to RNA-seq analysis.

The experimental results indicate that both the HFMM/PEG2 hydrogel and the LPS have caused an effect on the immune system process (GO:0002376) and defense function (GO:0006952) of the Raw264.7. After cells were co-cultured with the HFMM/PEG2 hydrogel, differential genes were more enriched to innate immune response (GO:0045067), indicating that the hyaluronic acid-based hydrogel of the present invention had a regulating effect on the innate immune response of Raw264.7. When LPS and HFMM/PEG2 hydrogel acted on the Raw264.7 simultaneously, the stimulation of LPS to Raw264.7 was still present; however, a portion of differential genes were enriched to biological processes negative regulation (GO:0048519). It indicates that the hyaluronic acid-based hydrogel of the present invention has a certain inhibiting effect on the cell function of LPS-induced Raw264.7. Furthermore, the expression of the inflammatory factor and chemokine-related genes (Ccl2, Ccl3, Ccl4, Ccl5, Ccl7, Mmp9, Cxcl10, Tnf, Il-1b, Il-1a, etc.), NF-κB pathway-related genes (Nfkbia, etc.), TLR-NOD pathway-related genes (Nod1, Nod2, Irf7, etc.), MAPK pathway-related genes (Mapk11, etc.) was remarkably down-regulated in the existence of the HFMM/PEG hydrogel, which indicates that the HFMM/PEG hydrogel plays an important role to the down-regulation of cell inflammatory factors.

The HUVEC in the culture flask were digested with a pancreatin, and inoculated onto a 6-well plate by 500,000/well, and cultured by an ECM endothelial medium for 24 h. The HFMM/PEG hydrogel synthesized in advance was placed into the well plate and co-cultured; equal volume of PBS was added to the control group, respectively. The cells were continuously cultured a day and subjected to RNA-seq analysis.

The experimental results indicate that the expression of the genes regulating cell adhesion (ICAM-1, COL1A1, TICAM-1, CALML4, etc.), MAPK pathway-related genes (MAPKAPK3, MAP3K5, etc.), and PI3K-AKT pathway angiogenic differentiation-related genes (VEGFA, AKT, SRC, RAC2, PTGS2, etc.) are enhanced remarkably, which proves that the hyaluronic acid-based hydrogel of the present invention plays an important role in promoting and maintaining the expression of the HUVEC angiogenic cells.

7.7 Variation of the Protein Levels of the Raw264.7 and HUVEC after being Co-Cultured with the Hydrogel Each group of cells were lysed with RIPA, a protease inhibitor and a phosphatase inhibitor were added at the same time to extract the total protein of the treated Raw264.7 and HUVEC. The protein was quantified by a BCA protein quantification kit; Loading buffer was added to boil the protein for 10 min at 100° C. Loading was conducted for Western Blot (WB). The experiment was conducted for 3 times.

The experimental results indicate that the hyaluronic acid-based hydrogel may accelerate the phosphorylation of p-ERK and p-JNK, activate the MAPK pathway, and accelerate the proliferation of the Raw264.7. In the existence of the hyaluronic acid-based hydrogel alone, the JNK pathway and the NF-κB pathway would be not inhibited remarkably. In the existence of LPS, the hyaluronic acid-based hydrogel may remarkably inhibit the expression of the MAPK pathways, i.e., p-ERK, p-MEK, and p-JNK, and remarkably inhibit the expression of the NF-κB pathways, i.e., p65, p-p65, and p-IKBα, and remarkably accelerate the expression of IKBα.

In addition, the hyaluronic acid-based hydrogel may activate the MAPK pathway and accelerate the proliferation of HUVEC by promoting the phosphorylation of p-ERK and the expression of ERK1/2; and may activate the PI3K-AKT pathway and accelerate the angiogenic capacity of HUVEC by promoting the phosphorylation of p-AKT and the expression of AKT.

In addition, this example further, by constructing a SD rat cranial defect model, proves that the hyaluronic acid-based hydrogel of the present invention has excellent capability to repair skin defect.

GelMA serves as the control group of this example and the reason is as follows: a hydrogel may be used as a scaffold material itself and thus has certain physical guidance on the repair of skin tissue defect; GelMA is selected as the material control group; the physical guidance of such a scaffold may be excluded during the experimental process, so as to prove that the hyaluronic acid-based hydrogel of the present invention may accelerate the healing of skin defect in each stage.

The performance test data of this example indicates as follows: the hyaluronic acid-based hydrogel of the present invention may remarkably promote the activity and proliferation of rBMSCs, significantly enhance the genetic expression of Raw264.7 Cd206, reduce the genetic expression of iNOS and Tnfα, increase the CD206 protein level, enhance the genetic expression of HUVEC ICAM-1, VCAM-1, VEGFA, and IL-8, increase the protein levels of PECAM-1 and ICAM-1, enhance the genetic expression of L929 Col1a1, decrease the expression of the TNFα-induced iNOS, increase the protein level of the COL1A1, reduce the protein level of the TNFα-induced iNOS, and inhibit the TNFα-induced L929 apoptosis. In the absence of LPS, the classical MAPK pathway is activated by enhancing the expression of p-ERK to promote the proliferation and the M2 polarization of macrophage. In the existence of LPS (simulating bacteriological environment), through the TLR-NOD-NF-κB-MAPK axis, the present invention may significantly inhibit the expression of MAPK pathways, p-ERK, p-MEK and p-JNK as well as the expression of NF-κB pathways, p65, p-p65 and p-IKBα, remarkably enhance the expression of IKBα, significantly inhibit the M1 polarization of macrophage, and meanwhile, continuously simulate the M2 polarization of macrophage. Furthermore, the hyaluronic acid-based hydrogel of the present invention may activate the MAPK pathway and accelerate the proliferation of HUVEC by enhancing the phosphorylation of p-ERK and the expression of ERK1/2; and may activate the PI3K-AKT pathway and accelerate the proliferation and vascularization of HUVEC by enhancing the phosphorylation of p-AKT and p-p85 and the expression of AKT.

Example 8

Transcriptome was utilized in this example to analyze and study the differential expression of genes in the cells after contacting with the hydrogel of the present invention, thus revealing the key mechanism. Pathway analysis shows that adhesion protein or connexin genes (e.g., integrin and cadherin) have more variations in osteogenesis, anti-inflammatory action, and angiogenesis processes. A and B of FIG. 25 show that ITGA6 (integrin subunit a6) has maximumly increased expression in rBMSC and Raw264.7; other molecules are down-regulated in varying degrees or increase to the minimum extent; in HUVEC, ITGA7 (integrin subunit a7) shows the maximumly increased expression quantity, and ITGA6 also shows increased expression quantity. ITGA6 and ITGA7 are paralogous genes encoding integrin pathway proteins. These genes may regulate the binding of protein-containing complex and laminin binding, and may serve as a receptor of laminin in mesenchymal cells and epithelial cells, and regulate the hemidesmosome, IGF signal transduction pathway, and MAPK signaling pathway. The expression of ITGA6 and ITGA7 are further validated by Western blot under RT-qPCR and HFMM/PEG hydrogels (C of FIG. 25). The ITGA6 level is related to the treatment degree of the HFMM/PEG hydrogel, indicating that ITGA6 will be a potential target.

Further, the level of intracellular ITGA6 is inhibited by the ITGA6 neutralizing antibody, GRGDSP integrin inhibitor, and short interfering RNA (siRNA); the results are shown in FIGS. 26 and 27. Results of FIGS. 26 and 27 show that after ITGA6 is inhibited in the hyaluronic acid-based hydrogel co-culture system, the osteogenic differentiation of rBMSC cells (FIG. 26)/anti-inflammatory ability of Raw264.77 cells (FIG. 27)/angiogenic capacity of HUVEC (B of FIG. 27) reduces significantly, which prompts that ITGA6 is a crucial molecule during the process of accelerating cell's osteogenic differentiation/anti-inflammation/angiogenesis by the hyaluronic acid-based hydrogel.

Obviously, the above examples of the present invention are merely cited to specify the present invention clearly, but are not construed as limiting the embodiments of the present invention. Those skilled in the art may make other different forms of changes or variations on the basis of the above description. All the embodiments are either not necessarily or cannot be exhaustive here. Any modification, equivalent replacement, improvement, and the like made within the spirit and principle of the present invention shall fall within the protection scope of the claims of the present invention.

What is claimed is:

1. A hyaluronic acid-based hydrogel precursor solution, comprising a component A and a component B, wherein the component A is prepared by the following steps:

step S1, mixing methacrylate group-modified hyaluronic acid with furfuryl amine for reaction, to obtain furan-methacrylate modified hyaluronic acid;

step S2, mixing the furan-methacrylate modified hyaluronic acid with maleimide for reaction, to obtain hyaluronic acid modified with dual groups; and step S3, mixing the hyaluronic acid modified with dual groups with a photoinitiator and a solvent, to obtain the component A;

wherein the component B is a mercapto polyethylene glycol solution, and a mass ratio of the hyaluronic acid modified with dual groups in the component A to the mercapto polyethylene glycol in the component B is 1:(2.5-5.0).

2. The hyaluronic acid-based hydrogel precursor solution according to claim 1, wherein a methacrylate group in the methacrylate group-modified hyaluronic acid of the step S1 has a degree of substitution of 25-35%.

3. The hyaluronic acid-based hydrogel precursor solution according to claim 1, wherein the step S1 has the following specific process:

dissolving the methacrylate group-modified hyaluronic acid into a morpholino-ethanesulfonic acid buffer solution first, adding 4-(4,6-dimethoxy-1,3,5-triazin-2-yl)-4-methylmorpholinium chloride, and adding the furfuryl amine, mixing and reacting for 20-24 h, and conducting dialysis, to obtain the furan-methacrylate modified hyaluronic acid.

4. The hyaluronic acid-based hydrogel precursor solution according to claim 1, wherein in the step S1, a furan group in the furan-methacrylate modified hyaluronic acid has a degree of substitution of 55-65%.

5. The hyaluronic acid-based hydrogel precursor solution according to claim 1, wherein the step S2 has the following specific process:

dissolving the furan-methacrylate modified hyaluronic acid into water, adding the maleimide, mixing and reacting for 20-24 h, and conducting dialysis, to obtain the hyaluronic acid modified with dual groups.

6. A hyaluronic acid-based hydrogel, wherein the hyaluronic acid-based hydrogel is obtained after gelatinizing the hyaluronic acid-based hydrogel precursor solution according to claim 1.

7. A repair material for treating a maxillofacial combined injury, comprising the hyaluronic acid-based hydrogel precursor solution according to claim 1.

8. The repair material according to claim 7, wherein the repair material is a bone defect repair material and/or a skin defect repair material.

9. The repair material according to claim 8, wherein the repair material is a bone defect repair material and/or a skin defect repair material for promoting the expression of ITGA6.

10. The repair material according to claim 7, wherein the repair material has a hemostatic function.

11. A repair material for treating a maxillofacial combined injury, comprising the hyaluronic acid-based hydrogel according to claim 6.

12. The repair material according to claim 11, wherein the repair material is a bone defect repair material and/or a skin defect repair material.

13. The repair material according to claim 12, wherein the repair material is a bone defect repair material and/or a skin defect repair material for promoting the expression of ITGA6.

14. The repair material according to claim 11, wherein the repair material has a hemostatic function.

* * * * *